(12) United States Patent
Madura et al.

(10) Patent No.: US 8,889,365 B2
(45) Date of Patent: Nov. 18, 2014

(54) METHODS AND KIT FOR DETECTING BREAST CANCER

(75) Inventors: Kiran Madura, Bridgewater, NJ (US); Li Chen, Hills Borough, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 377 days.

(21) Appl. No.: 13/204,947

(22) Filed: Aug. 8, 2011

(65) Prior Publication Data
US 2012/0028271 A1 Feb. 2, 2012

Related U.S. Application Data

(63) Continuation-in-part of application No. 11/908,691, filed as application No. PCT/US2006/009168 on Mar. 15, 2006, now Pat. No. 8,008,022.

(60) Provisional application No. 60/662,234, filed on Mar. 16, 2005.

(51) Int. Cl.
*G01N 33/574* (2006.01)

(52) U.S. Cl.
CPC .... *G01N 33/57411* (2013.01); *G01N 33/57415* (2013.01)
USPC ............................ 435/7.1; 435/7.25; 436/501

(58) Field of Classification Search
CPC .................................................. G01N 33/57415
USPC ............................ 435/7.1, 7.23; 436/501, 503
See application file for complete search history.

(56) References Cited

U.S. PATENT DOCUMENTS

| 5,744,343 | A | 4/1998 | Draetta et al. | ............. | 435/193 |
| 8,008,022 | B2 * | 8/2011 | Madura et al. | ............. | 435/7.1 |
| 2006/0234287 | A1 | 10/2006 | Erlander et al. | ............. | 435/6.14 |

OTHER PUBLICATIONS

Chuang, et al. (2005) Mol. Cell Biol. 25:403-413.*
Dapas et al. "Identification of Different Isoforms of eEF1A in the Nuclear Fraction of Human T-Lymphoblastic Cancer Cell Line Specifically Binding to Aptameric Cytotoxic GT Oligomers" European Journal of Biochemistry 2003 vol. 270:3215-3262.
Dragnev et al. "Specific Chemopreventive Agents Trigger Proteasomal Degradation of $G_1$ Cyclins: Implications for Combination Therapy" Clinical Cancer Research 2004 vol. 10:2570-2577.
Lamberti et al. "The Translation Elongation Factor 1A in Tumorigenesis, Signal Transduction and Apoptosis: Review Article" Amino Acids 2004 vol. 26:443-448.
Ohta, T. and Fukuda, M. "Ubiquitin and Breast Cancer" Oncogene 2004 vol. 23:2079-2088.
Rossi, S. and Loda, M. "The Role of Ubiquitination-Proteasome Pathway in Breast Cancer; Use of Mouse Models for Analyzing Ubiquitination Processes" Breast Cancer Research 2003 vol. 5(1):16-22.
Ruffner et al. "Cancer-Predisposing Mutations within the RING Domain of BRCA1: Loss of Ubiquitin Protein Ligase Activity and Protection from Radiation Hypersensitivity" Proceedings of the National Academy of Sciences of the United States of America 2001 vol. 98(9):5134-5139.
Thompson et al. "p62 Overexpression in Breast Tumors and Regulation by Prostate-derived Ets Factor in Breast Cancer Cells" Oncogene 2003 vol. 22:2322-2333.
Voorhees et al. "The Proteasome as a Target for Cancer Therapy" Clinical Cancer Research 2003 vol. 9:6316-6325.
Wyke et al. "Induction of Proteasome Expression in Skeletal Muscle is Attenuated by Inhibitors of NF-κB Activation" British Journal of Cancer 2004 vol. 91:1742-1750.
Yang et al. "Cancer Chemoprevention by Targeting Proteasomal Degradation" Clinical Cancer Research 2004 vol. 10:2220-2221.
Zhang et al. "Inhibitory Effect of Ubiquitin-Proteasome Pathway on Proliferation of Esophageal Carcinoma Cells" World Journal of Gastroenterology 2004 vol. 10(19):2779-2784.
Office Communication dated Jun. 1, 2010 from U.S. Appl. No. 11/908,691, filed Jul. 28, 2008, U.S. Patent No. 8,008,022.
Office Communication dated Aug. 12, 2010 from U.S. Appl. No. 11/908,691, filed Jul. 28, 2008, U.S. Patent No. 8,008,022.
Office Communication dated Nov. 26, 2010 from U.S. Appl. No. 11/908,691, filed Jul. 28, 2008, U.S. Patent No. 8,008,022.
Abbaszadegan et al. "Analysis of Multidrug Resistance-Associated Protein (*MRP*) Messenger RNA in Normal and Malignant Hematopoietic Cells" Cancer Research 1994 vol. 54:4676-4679.
Bowie et al. "Deciphering the Message in Protein Sequences: Tolerance to Amino Acid Substitutions" Science 1990 vol. 247:1306-1310.
Geng et al. "Binding Activity Difference of Anti-CD20 scFv-Fc Fusion Protein Derived from Variable Domain Exchange" Cellular & Molecular Immunology 2006 vol. 3(6):439-443.
Iehlé et al. "Differences in Steroid 5α-Reductase Iso-Enzymes Expression Between Normal and Pathological Human Prostate Tissue" The Journal of Steroid Biochemistry and Molecular Biology 1999 vol. 68:189-195.
Stanton et al. "Epidermal Growth Factor Receptor Expression by Human Squamous Cell Carcinomas of the Head and Neck, Cell Lines and Xenografts" British Journal of Cancer 1994 vol. 70:427-433.

* cited by examiner

*Primary Examiner* — Lynn Bristol
(74) *Attorney, Agent, or Firm* — Licata & Tyrrell P.C.

(57) ABSTRACT

The present inventions relates to kits and methods for diagnosing and monitoring breast cancer. An increase in the level or activity of proteins of the ubiquitin/proteasome pathway, and ancillary proteins thereof, as compared to normal control or benign tissue is indicative of breast cancer.

1 Claim, 1 Drawing Sheet

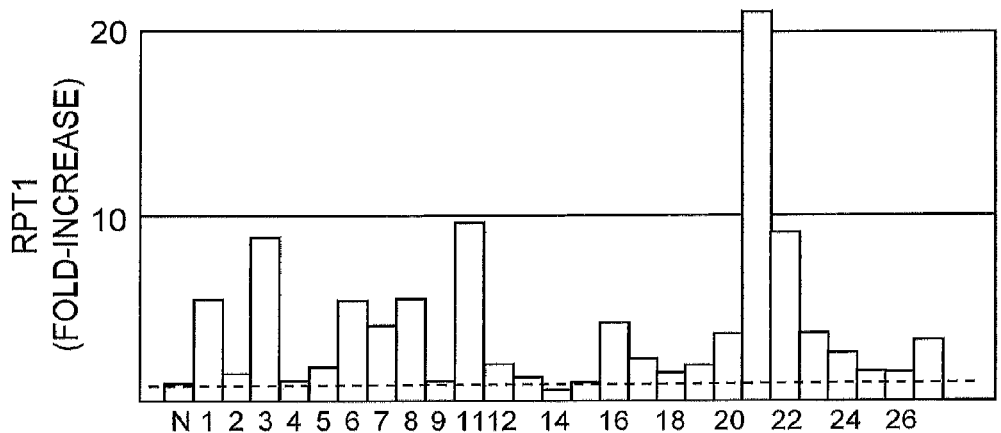

FIG. 1

MAVTITLKTLQQQTFKIRMEPDETVKVLKEKIEAEKGRDAFPVAGQKLIYAGKILS
M--QVTLKTLQQQTFKIDIDPEETVKALKEKIESEKGKDAFPVAGQKLIYAGKILN
M-VSLTFKNFKKEKVPLDLEPSNTILETKTKLAQSISCEESQIKLIYSGKVLQDSK
MSLNIHIKSGQDKWEVNVAPESTVLQFKEAINKANGIPVANQRLIYSGKILKDDQT

DDVPIRDYRIDEKNFVVVMVTKTK  -80  hHRAD23-A
DDTALKEYKIDEKNFVVVMVTKPK  -78  hHRAD23-B
TVSECGLKDGDQVVFMVSQKKSTK  -79  RAD23
VESYHIQDGHSVHLVKSQPKPQTA  -80  DSK2

FIG. 2

METHODS AND KIT FOR DETECTING BREAST CANCER

This application is a continuation-in-part application of U.S. Ser. No. 11/908,691, filed Jul. 28, 2008, now U.S. Pat. No. 8,008,022 which claims benefit of PCT/US2006/09168, filed Mar. 15, 2006 and U.S. Provisional Patent Application Ser. No. 60/662,234, filed Mar. 16, 2005, the contents of which are incorporated herein by reference in their entirety.

This invention was made with government support under Grant No. CA83875 awarded by the National Institutes of Health (NIH). The U.S. government has certain rights in this invention.

BACKGROUND OF THE INVENTION

The Ub/proteasome proteolytic pathway is required for efficient cell-cycle control, stress response, DNA repair, and differentiation (Glickman and Ciechanover (2002) *Physiol. Rev.* 82:373-428; Pickart (1997) *FASEB J.* 11:1055-1066; Varshaysky (1997) *Trends Biochem. Sci.* 22:383-387). Mutations in this pathway can cause pleiotropic defects because of its involvement in virtually all aspects of cell function. Consequently, the characterization of the Ub/proteasome pathway for the development of treatment for cancer and other malignancies is an area of active investigation (Voorhees, et al. (2003) *Clin. Cancer Res.* 9:6316-6325; Yang, et al. (2004) *Clin. Cancer Res.* 10:2570-7; Yang, et al. (2004) *Clin. Cancer Res.* 10:2220-2221; Rossi and Loda (2003) *Breast Cancer Res.* 5:16-22; Ohta and Fukuda (2004) *Oncogene* 23:2079-2088).

The 26S proteasome is composed of a catalytic (20S) particle and a regulatory (19S) particle. The structure and function of the 20S catalytic particle is conserved in evolution, and its compartmentalized organization ensures that the proteolytic activities are sequestered within the interior of the proteasome (Baumeister, et al. (1998) *Cell* 92:367-380). The large 19S regulatory particle interacts with the 20S particle to facilitate recognition, unfolding and degradation of ubiquitinated substrates (Glickman, et al. (1998) *Mol. Cell. Biol.* 18:3149-3162; Groll, et al. (2000) *Nat. Struct. Biol.* 7:1062-1067). Ubiquitin (Ub) is covalently attached to lysine sidechains in cellular proteins (Pickart (2000) *Trends Biochem. Sci.* 25:544-548). The ligation of Ub to proteins requires the action of three enzymes termed Ub-activating (E1), Ub-conjugating (E2), and Ub-ligases (E3) (Glickman and Ciechanover (2002) supra). The sequential addition of Ub moieties results in the formation of a multi-Ub chain, which facilitates protein degradation by promoting translocation of substrates to the proteasome (Gregori, et al. (1990) *J. Biol. Chem.* 265: 8354-8357; Thrower, et al. (2000) *EMBO J.* 19:94-102).

Malignant conditions are frequently associated with altered abundance and stability of regulatory proteins. It is therefore likely that the expression of a unique repertoire of proteins underlies the transition from normal to abnormal growth. Proteasome activity has been found to be elevated in esophageal cancer and cancer cachexia (Wyke, et al. (2004) *Br. J. Cancer* 91:1742-1750; Zhang, et al. (2004) *World J. Gastroenterol.* 10:2779-2784).

It has been shown that the co-translational degradation of newly synthesized misfolded proteins requires the Ub/proteasome system (Schubert, et al. (2000) *Nature* 404:770-774; Reits, et al. (2000) *Nature* 404:774-778; Turner and Varshaysky (2000) *Science* 289:2117-2220). Moreover, translation elongation factor 1-alpha (eEF1A) is required for the efficient degradation of nascent polypeptide chains, especially in ATP-depleting conditions, and in the presence of protein synthesis inhibitors (Chuang, et al. (2005) *Mol. Cell. Biol.* 25:403-413). eEF1A expression is increased in certain cancers, e.g, T-lymphoblastic cancer (Lamberti, et al. (2004) *Amino Acids* 26:443-448; Dapas, et al. (2003) *Eur. J. Biochem.* 270:3251-3262), a result that reflects a more general response to aberrant growth (Ejiri (2002) *Biosci. Biotechnol. Biochem.* 66:1-21).

BRCA1 and BRCA2 susceptibility factors have been linked to the Ub/proteasome pathway. BRCA1 contains a RING domain that binds Ub-conjugating enzymes and provides Ub-(E3) ligase activity (Cardoso, et al. (2004) *Clin. Breast Cancer* 5:148-157). The RING domain in BRCA1 can also bind a de-ubiquitinating enzyme, BAP1, and both proteins are coexpressed and colocalized (Orlowski, et al. (2003) *Breast Cancer Res.* 5:1-7). Mutations in the RING domain of BRCA1 abolishes its ability to function as an E3 ligase, and also blocks its interaction with BAP1, resulting in the loss of tumor suppressing properties of BRCA1. Moreover, the proteasome inhibitor, Velcade, has demonstrable efficacy in breast cancer (Ruffner, et al. (2001) *Proc. Natl. Acad. Sci. USA* 98:5134-5139; Hashizume, et al. (2001) *J. Biol. Chem.* 276:14537-14540).

Breast cancer represents one of the primary causes of death in women. This disease describes a range of defects, and the most prevalent forms include ductal carcinomas and local (in situ) or migrant (invasive/malignant) lobular-specific malignancies.

Prognosis for the patient is generally determined by the stage of advancement of the cancer. An important parameter that affects the type of treatment (mastectomy/chemotherapy/radiation therapy, etc.) is based on whether the cancer cells have infiltrated the lymphatic system. The aggregation of peripheral lymph nodes is considered an advanced state of disease. A critical and noteworthy fact is that breast cancer is eminently treatable, if it is detected early.

Currently, the most widespread methods for detection rely on breast self-examination and periodic mammography. However, a typical self-examination is imprecise, and it is unclear how faithfully the population adheres to the recommendation of monthly exams. Nonetheless, the self-exam can reveal abnormal growth of approximately one inch, while a mammogram can reveal smaller masses of aberrant growth.

Another non-invasive method that can detect smaller growths involves ultrasound. The feasibility of MRI-based approaches has also being investigated. Unfortunately, none of these methods is specific, since they do not distinguish between benign and cancerous growth. This is an important consideration because ~80% of biopsies are considered benign following pathological examination. Because early detection is critical for improving the prognosis for the patient, the availability of diagnostic methods that can identify abnormal growth early, and distinguish between cancer and non-malignant growth is crucial.

There is a general lack of biochemical and molecular methods for early diagnosis of breast cancer. Two methods that are currently available are based on polymerase chain reaction (PCR). For instance, the identification of mutations in the gene encoding the BRCA1 gene is currently in practice. However, these mutations, which are present in familial forms for breast cancer, affect fewer than 5% of patients. A second method is to measure the expression levels of the Her2 gene, which is indicative of increased potential for developing breast cancer. This marker is also representative of a minor fraction of patients. Since most incidence of breast cancer occur spontaneously, without a known genetic/familial origin, a proteomic method that can reveal altered expression of specific proteins, rather than genetic alterations (which affect only a subset of patients), is desirable. Ideally, the proteomic approach reveals changes in both familial and spontaneous classes of breast cancer. With a combination of genomic and proteomic diagnostic assays, early detection of breast cancer can become much more reliable and routine.

SUMMARY OF THE INVENTION

The present invention is a method for diagnosing breast cancer. The method involves determining the level or activity of UbcH5 and a protein of the immunoproteasome in a sample from a patient and comparing the determined level or activity with a control, wherein an increase in the level or activity of UbcH5 and a protein of the immunoproteasome in the sample as compared to the control is indicative of breast cancer. A kit for carrying out the diagnostic method is also provided.

BRIEF DESCRIPTION OF THE DRAWINGS

FIG. 1 shows the fold increase in Rpt1 protein levels in breast cancer tissue as compared to normal adjacent tissue (N).

FIG. 2 shows the amino acid sequence of UbL domains of hHRAD23-A (SEQ ID NO:1), hHRAD23-B (SEQ ID NO:2), RAD23 (SEQ ID NO:3), and DSK2 (SEQ ID NO:4). The positions of amino acid residues mutated herein (Lys7Ala, Thr79Pro and Pro77Thr) are indicated with arrows.

DETAILED DESCRIPTION OF THE INVENTION

Protein markers, whose expression and activity are strongly correlated with the incidence of breast cancer, have now been identified. These markers include proteins of the ubiquitin/proteasome pathway (e.g., ubiquitin-conjugating enzymes, UbcH5, UbcH2, UbcH1, and the immunoproteasome) and ancillary factors thereof (e.g., eEF1A). Tissue extracts displaying high proteasome activity were found to typically express higher levels of proteasome subunits, Ub-conjugating enzymes, eEF1A, and multiubiquitinated proteins. Taken together, 90% to 95% of the breast cancer samples were successfully identified by using these multiple parameters. Conversely, specimens that did not exhibit a significant change in proteasome activity showed no change in the levels of these factors. As a proteomic-based (and not genomic) assay was used to identify these markers, a much larger fraction of breast cancer patients can be detected. In contrast, the BRCA1 and Her2 PCR assays are useful diagnostic tools in only a small subset of patients. Accordingly, the present invention relates to markers and methods for diagnosing and monitoring breast cancer. Because the level of multiple proteins can be simultaneously examined using, e.g., antibody-based assays, the veracity of the instant assay is correspondingly strengthened.

To identify proteins whose expression levels were altered in breast cancer cells, a collection of human primary breast cancer specimens (25 individual samples) and corresponding patient-matched breast tissue control samples (normal adjacent tissue) were obtained. Patient age ranged from 35 to 89 years (with a median of 47 years), and a single sample was obtained from a 62-year-old male (sample 3). Tissues were homogenized and proteasome activity was determined using an equal amount of protein extracts. Proteasome activity for each breast cancer sample was adjusted to the activity that was present in patient-matched control specimens (that were set to an arbitrary value of 100). Significantly higher proteasome activity was detected in 23 of 25 positively diagnosed samples (P<0.001; Table 1). Only one specimen (sample 2) displayed reduced activity and a single isolate showed no significant change (sample 8). Because of the broad range in proteasome activity in the various patient tissue samples, subgroups were categorized and it was determined that only three specimens had <2-fold increased proteasome activity compared to the control tissue. Ten specimens displayed activity that was 2- to 5-fold higher than the patient-matched control (mean value ~3-fold increase; P<0.001), seven specimens had 5- to 10-fold higher levels (mean value~8-fold increase; P<0.001), and five specimens displayed a remarkable 10- to 35-fold elevated proteasome activity (mean value~20-fold increase; P<0.001). It was significant that two additional specimens, representing benign solid tumors, showed no increase in proteasome activity. Although both benign solid tumor samples contained very similar proteasome activities, only one specimen (see sample 9) was available with a patient-matched control sample, and therefore the second specimen (sample 10) was not plotted (Table 1).

TABLE 1

| Sample Number | Fold Increase in 26S Proteasome Activity |
|---|---|
| 1 | 12.00 |
| 2 | 0.58 |
| 3 | 5.39 |
| 4 | 1.84 |
| 5 | 2.88 |
| 6 | 16.00 |
| 7 | 3.68 |
| 8 | 1.22 |
| 9 | — |
| 10 | — |
| 11 | 27.6 |
| 12 | 4.39 |
| 13 | 3.11 |
| 14 | 2.54 |
| 15 | 2.76 |
| 16 | 31.58 |
| 17 | 8.98 |
| 18 | 2.48 |
| 19 | 8.17 |
| 20 | 2.18 |
| 21 | 9.66 |
| 22 | 5.57 |
| 23 | 7.00 |
| 24 | 8.64 |
| 25 | 2.54 |
| 26 | 4.25 |
| 27 | 12.61 |

—, indicates no change.

The observation that proteasome activity in benign tumors (samples 9 and 10) was indistinguishable from control levels indicates that the activity of the Ub/proteasome pathway is activated specifically in neoplastic cells. The basal proteasome activity in control tissues varied over a ~3-fold range (with an average value of 144±101), whereas the activity in 25 breast cancer specimens varied over an ~13-fold range (with an average value of 699±489). Therefore, absolute proteasome activity was increased ~5-fold in breast cancer (before correction against the patient-matched control tissue). Variance in activity measurements in cancer tissues was believed to reflect differences in disease stage, cellular origin of the malignancy, and condition of the tissue samples during and following collection. A pathology report that accompanied the tissue specimens provided the gender and patient's age, likely cellular origin, degree of infiltration, and the results of immunohistochemistry analysis. The majority of specimens (20 of 25) were derived from invasive ductal carcinomas (Infil DC), although one metastatic adenocarcinoma (Meta A), one intraductal carcinoma (Infil Intra DC), two lobular carcinoma (Infil LC), and one mucinous carcinoma (Meta C) were also examined (Table 2). The tissues were graded with regard to invasiveness and involvement of lymph nodes.

TABLE 2

| Sample | Age/Sex | Pathology Diagnosis | Grade/Differ. | Lymph Node |
|---|---|---|---|---|
| 1 | 47/F | Infil DC | High | – |
| 2 | 35/F | DC | High | – |
| 3 | 62/M | Infil DC | High/Poor | + |
| 4 | 42/F | Infil DC | High | + |
| 5 | 89/F | MC | Low | – |
| 6 | 65/F | Meta A | Medium | 1/11+ |
| 7 | 77/F | Infil DC | Medium | – |
| 8 | 40/F | Meta C | High | 3/7+ |
| 11 | NA/F | Infil DC | Medium/Poor | Vasc Inv |
| 12 | NA/F | In-situ DC | NA | 1/17+ |
| 13 | 58/F | Recurr Intra & Infil DC | High | Vasc |
| 14 | NA/F | Infil LC | NA | – |
| 15 | 72/F | Infil DC | NA | Metastase |
| 16 | 73/F | Infil DC | Poor | 13/16+ |
| 17 | 69/F | Infil LC | NA | 6/13+ |
| 18 | 38/F | Infil Intra DC | High | – |
| 19 | 40/F | Infil DC | High/Poor | 1/3+ |
| 20 | NA/F | Infil DC | Medium/Well | + |
| 21 | 49/F | Infil DC | Medium | – |
| 22 | 47/F | Infil DC | High/Poor | 7/14+ |
| 23 | 44/F | Infil DC | High | + |
| 24 | 41/F | Infil DA | Poor | Vasc Inv |
| 25 | 42/F | DC | High | + |
| 26 | 63/F | Infil DC | High/Poor | + |
| 27 | 41/F | Infil DC | High/Poor | + |

Vasc Inv, Vascular Invasive;
Vasc, Vascular;
NA, not available.

Hormone receptor status and Her2 antigenicity were also provided for these samples (Table 3).

TABLE 3

| Sample | Estrogen Receptor | Progesterone Receptor | Her2 |
|---|---|---|---|
| 1 | 30% | – | + |
| 2 | NA | NA | NA |
| 3 | 95% | 50% | – |
| 4 | 90% | 45% | – |
| 5 | 95% | 80% | – |
| 6 | NA | NA | NA |
| 7 | 95% | 45% | – |
| 8 | NA | NA | NA |
| 11 | 75% | 10-15% | + |
| 12 | NA | NA | NA |
| 13 | – | – | + |
| 14 | 95% | 95% | – |
| 15 | NA | NA | NA |
| 16 | – | – | – |
| 17 | 90% | 15% | – |
| 18 | 90% | 20-30% | + |
| 19 | 80% | + | + |
| 20 | 85% | 90% | + |
| 21 | 90% | 90% | – |
| 22 | 90% | 5-10% | + |
| 23 | NA | NA | NA |
| 24 | – | – | – |
| 25 | NA | NA | NA |
| 26 | 95% | 80% | – |
| 27 | NA | NA | NA |

Inspection of the data showed that the highest proteasome activities were observed in infiltrated ductal carcinomas, although the values among these specimens were highly variable, which could reflect the large sample size (n=20; mean increase=8-fold; P<0.001). High activity was also detected in one metastatic adenocarcinoma specimen (16-fold), whereas tissues displaying fibrocystic changes were not accompanied by a significant increase in proteasome activity (sample 9, ID-3576; sample 10, ID-3505). Results for some samples were unexpected. For example, sample 16 (ID-3353), which represented an infiltrating ductal carcinoma, displayed the highest proteasome activity (>30-fold) and high levels of UbcH5 (>40-fold) and eEF1A (>40-fold). These cells were poorly differentiated, and 13 of 16 lymph nodes were affected. This specimen was accompanied by low basal activity in control tissue. Yet, immunohistochemical analysis of these cells was entirely negative. Collectively, these data indicate that monitoring the activity of the Ub/proteasome pathway, and the expression of UbcH5 and eEF1A, provides important insight which complements conventional diagnostic approaches including pathology and histochemical inspection.

To determine if the elevated proteasome activity in breast cancer was the result of higher proteasome subunit expression, in contrast to post-translational activation (e.g., phosphorylation; Feng, et al. (2001) *Cell Growth Differ.* 12:29-37), protein extracts were resolved in an SDS-polyacrylamide gel and immunoblot analysis was carried out with antibodies against the proteasome subunit Rpt1, which is located in the 19S regulatory particle (Glickman, et al. (1998) supra). Consistent with the findings described here, higher levels of Rpt1 were detected in most samples that had higher proteasome activity (FIG. 1). The same immunoblots were subsequently incubated with antibodies against subunits in the 20S catalytic particle. As with Rpt1, increased levels of 20S subunits were detected in breast cancer specimens. The two benign tumor specimens (samples 9 and 10) did not display elevated levels of Rpt1. Furthermore, there was no single instance where the control sample had higher proteasome levels than the adjacent cancer tissue. However, the relationship between proteasome abundance and activity was not linear, indicating that other factors, such as post-translational modifications, could also increase proteasome activity. Higher Rpt1 levels were detected in 20 of 25 specimens, and only sample 8 displayed higher Rpt1 levels without a corresponding increase in proteasome activity. In contrast, samples 14 and 15 showed ~2.5-fold increased proteasome activity, without a change in Rpt1 levels, whereas sample 2 showed no increase in either abundance or activity. Further characterization of these samples showed higher eEF1A levels in specimen 15. Sample 8 is a notable exception in the set of 25 breast cancer specimens because it did not display higher proteasome activity or eEF1A levels (Table 4), although it expressed higher levels of UbcH5 (Table 4) and multi-Ub proteins. Collectively, these findings showed that by monitoring both proteasome activity, and abundance of UbcH5 and eEF1A, the majority of breast cancer specimens are successfully identified.

TABLE 4

| Sample Number | Fold Increase in eEF1A Expression | Fold Increase in UbcH5 Expression |
|---|---|---|
| 1 | 55.0 | 7.5 |
| 2 | 1.7 | 1.0 |
| 3 | 31.0 | 4.3 |
| 4 | 1.5-2.3 | 1.0-1.6 |
| 5 | 5.0 | 3.5 |
| 6 | 67.0 | 13.5 |
| 7 | 1.4 | 22.6 |
| 8 | 1.0 | 3.9 |
| 9 | n.d. | n.d. |
| 10 | n.d. | n.d. |
| 11 | 23.0 | 27.2 |

TABLE 4-continued

| Sample Number | Fold Increase in eEF1A Expression | Fold Increase in UbcH5 Expression |
|---|---|---|
| 12 | 2.7 | 1.3 |
| 13 | 2.0 | 1.8 |
| 14 | 1.0 | 1.0 |
| 15 | 2.6 | 3.6 |
| 16 | 44.0 | 44.0 |
| 17 | 29.0 | 10.7 |
| 18 | 4.5 | 8.9 |
| 19 | 14.2 | 7.1 |
| 20 | 15.5 | 2.6 |
| 21 | 12.6 | 1.6 |
| 22 | 69.0 | 17.5 |
| 23 | 37.0 | 6.1 |
| 24 | 3.9 | 6.1 |
| 25 | 1.8 | 3.7 |
| 26 | 4.2 | 7.7 |
| 27 | 11.0 | 3.0 |

Data were quantified using KODAK 1D densitometry software, and the magnitude of increase, compared with patient-matched controls is indicated.
n.d., not detected.

The majority of substrates that are degraded by the 26S proteasome are ligated to multi-Ub chains to promote targeting to the proteasome. If proteasome activity were related to the levels of proteolytic substrates, increased abundance of multiubiquitinated proteins in breast cancer tissues could be detected. Therefore, the levels of multiubiquitinated proteins in breast cancer tissue extracts were compared with control tissue extracts. Immunoblots were incubated with antibodies against Ub and higher levels of Ub were detected in breast cancer specimens 6, 7, 8, and 11. Similar results were observed in the majority of breast cancer samples. The levels of ubiquitinated proteins were not increased in specimen 5, consistent with the lower proteasome activity in this tissue specimen (Table 1). Specimens 9 and 10 represent benign solid tumor protein extracts and, in agreement with the results in Table 1, there was no evidence for higher levels of ubiquitinated proteins. The increased proteasome activity, and abundance of multiubiquitinated proteins in breast cancer tissues, reflects a cellular response to persistent and high levels of damaged (ubiquitinated) proteins. Because cancer cells are irrevocably changed, the increased proteasome activity and Ub abundance reflects a compensatory response to the altered cellular condition.

Based on the higher levels of multiubiquitinated proteins in breast cancer tissue extracts, it was determined if the levels of Ub-conjugating (E2) enzyme were altered. The Ubc4 class of E2 enzymes plays an important role in the turnover of damaged proteins, and the expression of this enzyme is rapidly induced in yeast, under conditions of stress (Tongaonkar and Madura (1998) *Anal. Biochem.* 260(2):135-41). Protein damage caused by heat stress and protein synthesis inhibitors results in rapid association between the proteasome and Ubc4 (Seufert and Jentsch (1990) *EMBO J.* 9:543-550). Because of the rapid proliferation of cancer cells, the expression of UbcH5 (the human counterpart of Ubc4) was analyzed in breast cancer tissue. Protein extracts were prepared from breast cancer and control samples, resolved in SDS-PAGE, and an immunoblot was incubated with antibodies against UbcH5. A marked increase in the levels of UbcH5 was observed in most breast cancer samples (Table 4). However, UbcH5 was not detected at higher levels in any of the control tissues or benign solid tumors. Many breast cancer samples displayed >8-fold higher levels of UbcH5, and specific specimens showed ~17-, 22-, 27-, and 44-fold higher levels. Specimen 4 was examined twice and comparable levels of UbcH5 were detected, demonstrating that the immunoblotting results were reproduced faithfully. In agreement with the earlier results, the failure to detect higher levels of UbcH5 in benign tumor tissue samples (samples 9 and 10) is consistent with the results in Table 1 and indicates that the activation of the Ub/proteasome pathway is indicative of neoplastic growth.

The levels of other Ub-conjugating enzymes, UbcH1 and UbcH2, were also analyzed in a subset of breast cancer tissue samples. Consistent with the results described herein, all specimens that showed higher levels of UbcH5 also displayed increased levels of UbcH1 and UbcH2. For instance, specimens 1, 3, and 6 showed higher proteasome activity, and increased expression of Rpt1, UbcH5, UbcH1, and UbcH2. Specimen 5 showed a moderate increase in the levels of E2 enzymes and proteasome subunits. Specimens 2 and 4 did not display increased proteasome activity, or higher levels of proteasome subunits and UbcH1/UbcH2. The expression of the same set of E2 enzymes was also analyzed in primary colon cancer tissue extracts and a consistent pattern of expression was not observed. Thus, E2 enzyme expression does not appear to be coordinately increased in colon cancer.

To further define other biomarkers of use in detecting breast cancer, 36 clinical breast cancer specimens were separated into 6 groups (Group 1=Specimens 4, 5, 10, 11, 15 and 25; Group 2=Specimens 26, 29, 34, 35, 37 and 147; Group 3=Specimens 150, 152-154, 156, 157, and 158; Group 4=Specimens 159, 168, 172, 179, 182 and 188; Group 5=Specimens 189, 191, 192, 195, 202 and 203; and Group 6=Specimens 204, 206, 213, 216, 218 and 220) and the level of candidate protein biomarkers was examined in protein extracts prepared from the specimens. The results of this analysis indicated that proteasome alpha-subunits showed a strong signal with no significant change observed among specimens, whereas proteins PA28α and UbcH5 showed strong signals in breast cancer samples. Protein levels correlated with either high or low levels of proteasome activity are listed in Table 5. The results of this analysis indicated that there was a strong correlation between proteasome activity and the levels of PA28 and UBCH5.

TABLE 5

| | | Sample # | | |
|---|---|---|---|---|
| Signal | Group | Proteasome Activity | PA28 Protein Level | UBCH5 Protein Level |
| High | 1 | 10, 25 | 11, 25 | 10, 25 |
| | 2 | 34, 37 | 34, 26 | 34, 37 |
| | 3 | 150, 154, 147 | 150, 154, 147 | 158, 154, 147 |
| | 4 | 168, 179 | 168, 179 | 168, 159 |
| | 5 | 192, 189 | 192, 189 | 192, 195 |
| | 6 | 213, 216, 204 | 213, 216, 204 | 213, 216, 204 |
| Low | 1 | 4, 15 | 5, 15 | 5, 15 |
| | 2 | 147 | 147 | 147 |
| | 3 | 156 | 156 | 156 |
| | 4 | 182 | 182 | 182 |
| | 5 | 202 | 202 | 202 |
| | 6 | 218, 220 | 218, 220 | 218, 220 |

The MCF10 cell line is recognized as a suitable model for breast cancer. Numerous derivatives of this cell line have been generated and reported to display varying degrees of tumorigenicity (Dawson, et al. (1996) *Am. J. Pathol.* 148:313-319; Santner, et al. (2001) *Breast Cancer Res. Treat.* 65:101-110; Giunciuglio, et al. (1995) *Int. J. Cancer* 63:815-822; Peng, et al. (2004) *Int. J. Oncol.* 25:961-971). Thus, it was determined whether a cell culture-based breast cancer model could provide an expeditious way to define the underlying role of the Ub/proteasome pathway in cancer. A set of cell lines that have been used to model breast cancer (MCF10A, MCF10AT1, MCF10DCIS.COM, and MCF10CA1a) were analyzed. Total protein extracts were prepared, and proteasome activity and abundance were measured. All four cell lines, which represented an untransformed strain, and three distinct lineages with unique tumorigenicity properties, displayed similar proteasome activity. Furthermore, immunoblot analysis showed that the levels of proteasome subunits (Rpn2, Rpt1, and 20S α-subunits) were similar in all the cell lines. Immunoblots were also incubated with antibodies against UbcH5 and eEF1A, and, as above, no difference in expression levels was detected in these cell lines. These unexpected results underscore the importance of examining primary cancer tissue samples for defining the biochemical changes that accompany breast cancer. Although others have reported that MCF10-derived cells display properties consistent with transformed cells (Santner, et al. (2001) supra), none of the biochemical alterations observed herein in primary tissues were detected in this cell culture model. Levels of BRCA1 have been shown to be similar in both growth-arrested and rapidly proliferating MCF10A cells, leading to the conclusion that this tumor suppressor might not control cell cycle progression in breast cancer cells (Aprelikova, et al. (1996) *Oncogene* 13:2487-2491). However, an alternative interpretation, based on the studies described here, this cell culture-based model system might not faithfully reflect all the biochemical changes that underlie breast cancer progression in primary tissues.

It has been demonstrated that 30% to 50% of nascent proteins are degraded before they mature (Schubert, et al. (2000) supra; Reits, et al. (2000) supra; Turner and Varshavsky (2000) supra). Thus, the major fraction of substrates of the proteasome is likely to originate from the ribosome. Cancer cells are metabolically active and are engaged in active protein synthesis. Translational elongation factor eEF1A is known to form a specific interaction with ubiquitinated nascent proteins and the proteasome in the presence of protein synthesis inhibitors (Chuang, et al. (2005) supra). Based on the increased activity of the proteasome, and higher levels of proteasome subunits, Ub-conjugating enzymes and multiubiquitinated proteins in breast cancer tissue samples, it was determined whether eEF1A levels were correspondingly increased. Increased expression of eEF1A in breast cancer would suggest the presence of high levels of nascent, damaged proteins. Protein extracts were examined by immunoblot analysis, and increased levels of eEF1A were detected in most breast cancer specimens (Table 4). The increased level of eEF1A in cancers such as T-lymphoblastic cancer has been described (Lamberti, et al. (2004) supra; Dapas, et al. (2003) supra), and the results shown here indicate that a common cellular response to protein damage might occur during hyperproliferation in breast and other cancers. Although malignant cells are metabolically very active, the dramatically higher levels of eEF1A (30- to 67-fold increased levels in certain specimens) cannot be explained solely by a requirement for increased protein synthesis in metabolically active, neoplastic cells. It is believed that the increased abundance of eEF1A reflects its role in the turnover of high levels of nascent damaged proteins. As noted, no change in eEF1A levels was detected in benign solid tumors, confirming that the expression and activity of the Ub/proteasome pathway and its ancillary factors are elevated specifically in primary breast cancer cells in humans with breast cancer relative cancer-free breast tissue.

To further analyze the dynamics of the Ub/proteasome pathway, hHR23A and hHR23B interactions with proteasomes and multiubiquitinated proteins, and other cellular factors were determined. hHR23A and hHR23B, homologs of Rad23, contain an amino-terminal ubiquitin-like (UbL) domain that can bind the proteasome, and two ubiquitin-associated (UBA) domains that bind Ub, multi-Ub chains, and multiubiquitinated substrates. UbL/proteasome binding is required in vivo, and promotes efficient DNA repair in a reconstituted system.

To examine the conservation in Rad23 biochemical function, UbL domains from yeast Rad23 (residues 1-78) and Dsk2 (1-78), and human hHR23A (1-79) and hHR23B (1-78) were expressed and purified from yeast cells. Protein extracts were applied to glutathione-SEPHAROSE™, and a strong interaction with the proteasome was detected with the UbL domain from yeast Rad23. No interaction was observed with GST, or ubiquitin, since mono-Ub does not show appreciable affinity for the proteasome (Thrower, et al. (2000) *EMBO J.* 19:94-102). The UbL domain of yeast Dsk2 also showed weak interaction, consistent with previous findings (Walters, et al. (2002) *Biochemistry* 41:1767-77). Despite significant sequence similarity (~75%) between human UbL-hHR23A and UbL-hHR23B (referred to herein also as UbL-A and UbL-B, respectively), only the latter interacted with the yeast proteasome. Because the two human Rad23 proteins are functionally redundant in DNA repair, their distinct cross-species interactions with yeast proteasomes indicated that they might mediate different functions in protein degradation. Therefore, human cell extracts were analyzed.

Protein extracts were prepared from cultured cell lines, and applied to GST-UbL-A and GST-UbL-B, to compare their interaction with the proteasome. Following incubation with protein extracts that were prepared from MCF10A, Hut78 and CHO cells, higher levels of Rpt1, Rpn2 and alpha-proteasome subunits were consistently found associated with GST-UbL-B. Furthermore, higher chymotryptic activity was purified with GST-UbL-B, in agreement with the increased binding to the proteasome. Similar findings were observed in ZR-75-1 breast cancer cells. Addition of epoxomicin completely inhibited the chymotryptic activity, confirming the specificity of the proteasome assay. The results from 14 independent measurements were standardized to the activity purified with UbL-A. Although Ponceau S staining showed equal amounts of GST-UbL-A and GST-UbL-B on the affinity beads, ~3-fold higher levels of proteasomes were observed with UbL-B (mean 2.94±1.01; P<0.001). Collectively, these results indicate that the distinct proteasome-binding properties of UbL-A and UbL-B are related to distinct functions in vivo, and not caused by cell-line specific effects.

It has been suggested that an intramolecular interaction with a UBA domain might prevent the UbL domain in Rad23 from binding the proteasome (Walters, et al. (2002) supra). Therefore to determine if full-length hHR23 protein would reproduce the binding properties of purified UbL domains, full-length GST-tagged hHR23A and hHR23B were immobilized and incubated with protein extracts prepared from Hut78 cells. Significantly higher levels of proteasome subunits in association with hHR23B were detected, consistent with the results obtained with purified UbL domains. The associated chymotrypsin-like activity was also measured and approximately 2-fold higher levels were detected with hHR23B. The data from 10 independent measurements were averaged and plotted (mean 2.39±0.98; P<0.001).

Understanding the significance of Rad23 interaction with ubiquitinated proteins and the proteasome facilitates the elucidation of its biological functions (Chen and Madura (2002) *Mol. Cell. Biol.* 22:4902-13; Elsasser, et al. (2004) *J. Biol. Chem.* 279:26817-22; Verma, et al. (2004) *Cell* 118:99-110;

Kim, et al. (2004) *Mol. Biol. Cell* 15:3357-65; Saeki, et al. (2002) *Biochem. Biophys. Res. Commun.* 293:986-92). Rad23 proteins contain two ubiquitin-associated (UBA) domains that can bind multiubiquitin chains, and ubiquitinated substrates (Bertolaet, et al. (2001) *Nat. Struct. Biol.* 8:417-22; Wilkinson, et al. (2001) *Nat. Cell Biol.* 3:939-43). The amino-terminal UBA1 domain forms a stronger interaction with multi-Ub chains, than the carboxy-terminal UBA2 domain, although both domains are required for maximal binding to ubiquitinated proteins (Chen and Madura (2002) supra). The interaction between cellular multiubiquitinated (multi-Ub) proteins and full-length hHR23 proteins was determined, as were UBA domains that were derived from hHR23A and hHR23B. Immunoblot analysis with anti-ubiquitin antibodies revealed a unique pattern of interaction with hHR23A and hHR23B. hHR23A and UBA1-A showed reproducibly increased binding to high molecular weight multi-Ub proteins, compared to hHR23B and UBA1-B. These data were quantified, and it was determined that hHR23A formed >2-fold increased interaction with multi-Ub proteins, compared to hHR23B. Furthermore, the multi-Ub species bound to hHR23A displayed a noticeably higher molecular weight distribution than the species bound to hHR23B. Taken together, the unique proteasome and multi-Ub binding properties of hHR23A and hHR23B indicate that they have unique functions.

Mutation of lysine-7 in the UbL domain of yeast Rad23 is known to abolish its interaction with the proteasome (Kim, et al. (2004) supra). Thus, similar mutations in human UbL-A and UbL-B were generated (UbL-A$^{K8A}$ and UbL-B$^{K6A}$, FIG. 2), and the interaction of the resulting mutants with the proteasome was examined. Equivalent amounts of the purified GST-UbL mutant proteins UbL-A$^{K8A}$ and UbL-B$^{K6A}$ were incubated with cell extracts, and the interaction with the proteasome, and associated hydrolytic activity were determined. Consistent with previous results, mutation of the residue corresponding to lysine-7 in yeast Rad23 abolished proteasome binding by both human UbL-A and UbL-B, and resulted in dramatically reduced proteasome-specific activity. Further, the distinct proteasome-binding properties of the unmutated UbL-A and UbL-B domains were confirmed. Significantly lower levels of Rpn2, Rpt1, and alpha subunits were purified with UbL-A.

To verify that the reduced proteasome-binding by UbL-A was not the result of an unforeseen structural defect, its interaction with Ataxin-3 was examined using the same immunoblots. Ataxin-3 bears similarity to S5a, a proteasome subunit that binds multiubiquitinated proteins (Deveraux, et al. (1994) *J. Biol. Chem.* 269:7059-7061), and UbL domains in Rad23 proteins (Wang, et al. (2000) *Hum. Mol. Genet.* 9:1795-803). Similarly, Ataxin-3 can bind the UbL domains in both human Rad23 proteins (Wang, et al. (2000) supra), and might also encode a proteasome-associated factor that binds multiubiquitinated proteins (Doss-Pepe, et al. (2003) *Mol. Cell. Biol.* 23:6469-83). An immunoblot was incubated with antibodies against Ataxin-3 and equivalent binding was observed for both UbL-A and UbL-B, demonstrating that the UbL domains were not structurally defective. These results show that distinct residues in UbL contribute to binding Ataxin-3 and the proteasome.

Binding between Ataxin-3 and full-length hHR23A and hHR23B was also compared. GST-hHR23A and GST-hHR23B were incubated with protein extracts and differential binding to the proteasome was observed. GST-hHR23A was associated with reduced proteasome activity, whereas the interaction with Ataxin-3 was similar for hHR23A and hHR23B.

The amino acid sequences of UbL-A and UbL-B are highly conserved, despite their dissimilar proteasome-binding properties. A conspicuous difference between UbL-A and -B is the presence of additional amino-terminal residues in UbL-A (FIG. 2). To determine if these residues inhibited interaction with the proteasome, a UbL-A derivative that lacked the additional amino terminal residues (Ala-2 and Val-3) was generated. Removal of these residues and conversion of several other residues in UbL-A did not increase interaction with the proteasome. However, the cloning design of the GST-UbL fusion proteins fortuitously generated a sequence that terminated after 72-Val-Val-Val-Met-Val-Thr-Lys-Thr-79 (SEQ ID NO:5) in UbL-A$^{1-79}$, and 72-Val-Val-Val-Met-Val-Thr-Lys-Pro-Lys-78 (SEQ ID NO:6) in UbL-B$^{1-78}$. To determine if the different carboxy-termini might affect proteasome-interaction, new constructs were prepared that terminated with the same carboxy-terminal residue (Val-Val-Val-Met-Val-Thr-Lys (SEQ ID NO:7); UbL-A$^{1-78}$ and UbL-B$^{1-76}$). It was determined that UbL-A$^{1-78}$ interaction with the proteasome and the associated chymotryptic activity were significantly increased. The values from five independent measurements were plotted (mean increase 2.5±0.25; P<0.001). In contrast, proteasome-interaction by UbL-B$^{1-76}$ was unchanged, and remained high. Although the average values for UbL-A$^{1-78}$ were not as high as UbL-B$^{1-76}$, the difference was not significant (P>0.05). All UbL derivatives formed an equivalent interaction with Ataxin-3, demonstrating that Ataxin-3 and proteasome binding are separate effects.

Threonine-79 in hHR23A was also converted to a proline residue (Thr79Pro), which is present in hHR23B, to confirm that the full-length protein would mirror the proteasome binding properties of the isolated UbL domains (see arrow in FIG. 2). Higher amounts of proteasome subunits (Rpn2 and Rpn1) were co-purified with GST-hHR23AP$^{T79P}$ while the interaction with Ataxin-3 was unaffected. Chymotryptic activity associated with GST-hHR21A$^{T79P}$, GST-hHR23A and GST-hHR23B was measured and significantly higher activity was detected with hHR23AP$^{T79P}$, compared to hHR23A (P<0.01). In contrast, the activity associated with hHR23AP$^{T79P}$ was not as high as that detected with GST-hHR23B, although the difference was not significant (P>0.05). These results showed that a single amino acid residue, present at the junction between UbL-A and downstream sequences of hHR23A, significantly affected proteasome binding. Moreover, a reciprocal substitution in hHR23B, in which Pro-77 was replaced with Thr-77 (GST-hHR23B$^{P77T}$), did not reduce proteasome binding and chymotryptic activity to the levels observed with hHR23A, indicating that the negative effect of Thr-79 in hHR23A, may involve other residues in UbL-A. It was also noted that conversion of hHR23-A to a stronger proteasome-interacting factor (hHR23A$^{T79P}$), did not affect its association with multi-Ub protein. These results are consistent with established observations that Rad23 interactions with the proteasome and multi-Ub proteins are separable functions (Chen and Madura (2002) supra).

The biological function of a protein can be understood through the identification of its physiological partners. Thus, affinity matrices containing the UbL domains from hHR23A and hHR23B were prepared and incubated with protein extracts prepared from primary human breast cancer and normal adjacent tissue (NAT) specimens. The bound proteins were released, resolved in polyacrylamide gels, and stained with COOMASSIE blue. In addition to proteasome subunits, a novel pattern of binding factors were detected in breast cancer protein extracts. Protein bands were excised and identified by mass spectrometry, and the identity of a subset of UbL-binding proteins was identified. UbL-A precipitated Ub-activating enzyme E1, Ub-isopeptidase T, several translation elongation factors (e.g., EF2) and a human homolog of mouse mKIAA0467 (GENBANK Accession No. BAC97962). Significant levels of the stress-inducible factor Hsp71 were also detected in association with UbL-A. In contrast, UbL-B was purified with various forms of the structural protein vimentin. Native vimentin is an ~58 kDa protein, and the higher molecular weight forms that were associated with UbL-B could represent filaments. It was also noted that UbL-A precipitated BRCA2 fragments, while BRCA1 breakdown products were isolated with UbL-B. There is evidence that BRCA1 is targeted for degradation by the Ub/proteasome pathway (Choudhury, et al. (2004) *J. Biol. Chem.* 279:33909-18; Choi (2001) *Int. J. Oncol.* 19:687-93), and BRCA2 has been reported to be ubiquitinated (Schoenfeld, et al. (2004) *Mol. Cell. Biol.* 24:7444-55). Although both UbL-A and UbL-B can bind the proteasome, it is contemplated that the binding proteins identified herein represent proteins that are targeted to the proteasome.

To verify the proteomic analysis, GST-UbL fusion proteins were incubated with cell extracts, and immunoblots were reacted with antibodies against vimentin. Consistent with the proteomic analysis, a predominant interaction was observed with UbL-B. In contrast, incubation with antibodies against translation elongation factor 1A (eEF1A), showed strong interaction with UbL-A, and significantly reduced binding to UbL-B. Collectively, these studies confirmed the proteomic analysis, and indicate that human Rad23 proteins have unique partners in vivo and can each be used to identify novel biomarkers in breast cancer tissues.

Accordingly, the present invention relates to the Ub/proteasome pathway and ancillary proteins or nucleic acids encoding such proteins for use as markers in the diagnosis and monitoring of breast cancer. For example, the marker proteins and binding moieties, for example, antibodies that bind to the marker proteins or nucleic acid probes which hybridize to nucleic acid sequences encoding the marker proteins, can be used to detect the presence of breast cancer in an individual.

As used herein, breast cancer is understood to mean any cancer or cancerous lesion associated with breast tissue and can include precursors to breast cancer, for example, atypical ductal hyperplasia or non-atypical hyperplasia. It is not necessary that the marker protein be unique to a breast cancer tissue or sample of an individual afflicted with breast cancer; rather the marker protein should have a signal to noise ratio high enough to discriminate between samples originating from a breast cancer sample and samples originating from normal breast tissue.

Marker proteins of the present invention were identified by comparing the protein composition of a breast cancer tissue sample with the protein composition of a patient-matched breast tissue control sample. Marker proteins identified and embraced by the present invention include those of the human Ub/proteasome pathway and ancillary proteins thereof. As used herein, a protein of the Ub/proteasome pathway is a protein of the 26S proteasome, proteasome ancillary factors as well as proteins involved in the covalent attachment of ubiquitin to cellular proteins (e.g., Ub-activating enzymes, Ub-conjugating enzymes, and Ub-ligases) thereby facilitating protein degradation. The 26S proteasome is composed of a 700-kD 20S proteasome catalytic core proteinase and two 19S regulatory modules.

The 20S core is made up of four rings of 14 pairs of non-identical subunits; two rings are composed of seven alpha subunits and two rings are composed of seven beta subunits. Proteins of the human 20S proteasome include, e.g., alpha subunits PSMA1 (GENBANK Accession No. NM_002786), PSMA2 (GENBANK Accession No. NM_002787), PSMA3 (GENBANK Accession No. NM_002788), PSMA4 (GENBANK Accession No. NM_002789), PSMA5 (GENBANK Accession No. NM_002790), PSMA6 (GENBANK Accession No. NM_002740), and PSMA7 (GENBANK Accession No. NM_152255); and beta subunits, e.g., PSMB1 (GENBANK Accession No. NM_002793), PSMB10 (GENBANK Accession No. NM_002801), PSMB2 (GENBANK Accession No. NM_002794), PSMB3 (GENBANK Accession No. NM_002795), PSMB4 (GENBANK Accession No. NM_002796), PSMB5 (GENBANK Accession No. NM_002797), PSMB6 (GENBANK Accession No. NM_012217), PSMB7 (GENBANK Accession No. NM_002799), PSMB8 (GENBANK Accession No. NM_148919), and PSMB9 (GENBANK Accession No. NM_002800).

The 19S regulator is composed of a base, which contains six ATPase subunits and two non-ATPase subunits, and a lid, which contains up to 10 non-ATPase subunits. Each of the 6 ATPases, namely PSMC1 (GENBANK Accession No. NM_002802), PSMC2 (i.e., rpt1; GENBANK Accession No. NM_002803), PSMC3 (GENBANK Accession No. NM_002804), PSMC4 (GENBANK Accession No. NM_006503), PSMC5 (GENBANK Accession No. NM_002805), and PSMC6 (GENBANK Accession No. NM_002806), contain an approximately 230-amino acid AAA (ATPases associated with diverse cellular activities) domain (Tanahashi, et al. (1998) *Biochem. Biophys. Res. Commun.* 243: 229-232). The non-ATPase polypeptides of the 19S regulatory complex include, e.g., PSMD1 (i.e., rpn2; GENBANK Accession No. NM_002807), PSMD2 (GENBANK Accession No. NM_002808), PSMD3 (GENBANK Accession No. NM_002809), PSMD4 (GENBANK Accession No. NM_002810), PSMD5 (GENBANK Accession No. NM_005047), PSMD6 (GENBANK Accession No. NM_014814), PSMD7 (GENBANK Accession No. NM_002811), PSMD8 (GENBANK Accession No. NM_002812), PSMD9 (GENBANK Accession No. NM_002813), PSMD10 (GENBANK Accession No. NM_002814), PSMD11 (GENBANK Accession No. NM_002815), PSMD12 (GENBANK Accession No. NM_002816), PSMD13 (GENBANK Accession No. NM_002817), and PSMD14 (GENBANK Accession No. NM_005805).

A modified proteasome, referred to as the immunoproteasome, processes class I MHC peptides. The immunoproteasome contains an alternate regulator, referred to as the 11S regulator or PA28, that replaces the 19S regulator. Three subunits, alpha (PSME1, GENBANK Accession No. NM_006263), beta (PSME2, GENBANK Accession No. NM_002818) and gamma (PSME3, GENBANK Accession No. NM_005789) of the 11S regulator have been identified.

Other proteins of the ubiquitin pathway include ubiquitin activating enzymes (i.e., E1s) such as UBE1 (GENBANK Accession Nos. NM_153280 and NM_003334), UBE1L (GENBANK Accession No. NM_003335), UBE1C (GENBANK Accession Nos. NM_198197, NM_198195, and NM_00396); ubiquitin conjugating enzymes (i.e., E2s) such as UBE2E3 (GENBANK Accession Nos. NM_006357 and NM_182678), UBE2G1 (GENBANK Accession Nos. NM_182682 and NM_003342), UBE2L6 (GENBANK Accession Nos. NM_198183 and NM_004223), UBE2L3 (GENBANK Accession Nos. NM_003347 and NM_198157), UBE2N (GENBANK Accession No. NM_003348), UBE2M (GENBANK Accession No. NM_003969), UBE2J2 (GENBANK Accession Nos.

NM__194458, NM__194457, NM__194315, and NM__058167), UBE2J1 (GENBANK Accession No. NM__016021), UBE2H (i.e., UbcH2, GENBANK Accession Nos. NM__003344 and NM__182697), UBE2D2 (GENBANK Accession Nos. NM__003339 and NM__181838), UBE2D3 (GENBANK Accession Nos. NM__181886, NM__003340, and NM__181887), UBE2B (GENBANK Accession No. NM__003337), UBE2D1 (i.e., UbcH5, GENBANK Accession No. NM__003338), and UBE2K (i.e., UbcH1, GENBANK Accession No. NM__005339); ubiquitin ligases (i.e., E3s) such as UBE3B (GENBANK Accession Nos. NM__130466, NM__183414 and NM__183415); and ubiquitin isopeptidase T (GENBANK Accession No. NM__003481). Particular embodiments of the present invention exclude BRCA proteins as markers.

Many proteins must undergo post-translational modification such as phosphorylation, methylation or oxidation, or associate with molecular chaperones prior to recognition by the appropriate ubiquitin ligase of the Ub/proteasome pathway. Thus, the present invention also provides such ancillary proteins of the ubiquitin/proteasome pathway as markers for use in the methods and kit of the present invention. Exemplary ancillary proteins include, e.g., human eEF1A (GENBANK Accession No. NM__001402), human eEF2 (GENBANK Accession No. NM__001961), HSP71 (GENBANK Accession No. NM__006597), and VCP/p97 (GENBANK Accession No. NM__007126).

While any of the above-referenced Ub/proteasome pathway and ancillary marker proteins can be used in accordance with the methods and kit disclosed herein, particular embodiments embrace the use of one, two, three, four or more of the following: PSMC2, also referred to herein as rpt1 (SEQ ID NO:8; see GENBANK Accession No. NM__002803); PSMD1, also referred to herein as rpn2 (SEQ ID NO:9; see GENBANK Accession No. NM__002807); UBE2H also referred to herein as UbcH2 (SEQ ID NO:10, see GENBANK Accession Nos. NM__003344 and NM__182697); UBE2D1, also referred to herein as UbcH5 (SEQ ID NO:11, see GENBANK Accession No. NM__003338); UBE2K, also referred to herein as UbcH1 (SEQ ID NO:12, see GENBANK Accession No. NM__005339), subunits of the PA28, and eEF1A (SEQ ID NO:13, see GENBANK Accession No. NM__001402).

Marker proteins useful in the present invention encompass not only the particular sequences identified herein but also others identified by, e.g., binding to hRAD23-A (GENBANK Accession No. NM__005053) or hRAD23-B (GENBANK Accession No. NM__002874) proteins, or UbL domains thereof. Moreover, allelic variants of the markers disclosed herein are also contemplated. Thus, for example, sequences that result from alternative splice forms, post-translational modification, or gene duplication are each encompassed by the present invention. Species variants are also encompassed by this invention where the patient is a non-human mammal. Preferably, variant sequences are at least 80% similar or 70% identical, more preferably at least 90% similar or 80% identical, and most preferably 95% similar or 90% identical to at least a portion of one of the sequences disclosed herein. As used herein, a "portion" or a "fragment" denotes a contiguous peptide or nucleic acid containing at least 10, 20, 30, 40 or 50 amino acids or nucleic acids from the reference protein or nucleic acid sequence. To determine whether a candidate peptide region has the requisite percentage similarity or identity to a reference polypeptide, the candidate amino acid sequence and the reference amino acid sequence are first aligned using a dynamic programming algorithm, e.g., described by Smith and Waterman ((1981) *J. Mol. Biol.* 147: 195-197), in combination with the BLOSUM62 substitution matrix described by Henikoff and Henikoff ((1992) *Proc. Natl. Acad. Sci. USA* 89:10915-10919). For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art. Once the alignment between the candidate and reference sequence is made, a percent similarity score is calculated. The individual amino acids of each sequence are compared sequentially according to their similarity to each other.

Marker proteins in a sample can be detected via binding assays, wherein a binding moiety which specifically binds the marker protein (i.e., a binding partner for the marker) is introduced into a sample suspected of containing the marker protein. In such an assay, the binding partner is generally detectably labeled as, for example, with a radioisotopic or fluorescent marker. Labeled antibodies can be used in a similar manner in order to isolate selected marker proteins. Nucleic acids encoding marker proteins are detected using nucleic acid probes having a sequence complementary to at least a portion of the sequence encoding the marker protein. Techniques such as PCR and, in particular, reverse transcriptase PCR, are useful means for isolating nucleic acids encoding a marker protein.

Using the instant marker proteins or nucleic acids encoding the proteins, the skilled artisan can use any one of a variety of detection methods for diagnosing or monitoring breast cancer in a human. The methods typically employ the steps of determining, by some means, the level of one or more Ub/proteasome pathway marker protein or nucleic acids encoding such protein in a tissue sample (e.g., an aspirated breast cell sample or biopsy sample) or bodily fluid (e.g., blood, spinal fluid, urine, or breast milk) and comparing said level to that of the marker protein or nucleic acid in a control sample to determine whether there is a detectable increase (e.g., 1.5-fold or more) in the level of the marker protein or nucleic acid encoding such protein in the sample which is indicative of breast cancer. The test sample can be obtained from a subject exhibiting signs or symptoms of breast cancer (e.g., lumps) or a subject at risk of having breast cancer (e.g., a subject with a family history or a subject who has had breast cancer in the past and is at risk of recurrence). As such, the methods of the invention are useful for selecting a suitable therapeutic course of treatment. In particular embodiments, the accuracy and/or reliability of the instant methods is further enhanced by determining the level or activity of a plurality of Ub/proteasome pathway marker proteins and/or nucleic acids in the sample. Assays for determining the level or activity of marker proteins can be protein-based or nucleic acid-based.

In a protein-based assay, the level of marker protein in a sample is determined, for example, by combining the marker protein with an antibody-based binding moiety capable of specifically binding the marker protein. An antibody-based binding moiety of the present invention is intended to include an antibody, antibody fragment or antibody derivative. Binding proteins can also be designed which have enhanced affinity for a target protein. Optionally, the binding moiety can be linked with a detectable label, such as an enzymatic, fluorescent, radioactive, phosphorescent or colored particle label. The labeled complex is detected, e.g., visually or with the aid of a spectrophotometer or other detector.

Levels of marker proteins can also be determined using one- or two-dimensional gel electrophoresis techniques available in the art. In two-dimensional gel electrophoresis, the proteins are separated first in a pH gradient gel according to their isoelectric point. The resulting gel then is placed on a second polyacrylamide gel, and the proteins separated according to molecular weight (see, for example, O'Farrell (1975) *J. Biol. Chem.* 250:4007-4021). In accordance with two-dimensional gel electrophoresis analysis, one or more marker proteins are detected by first isolating proteins from a sample obtained from an individual suspected of having breast cancer, and then separating the proteins by two-dimensional gel electrophoresis to produce a characteristic two-dimensional gel electrophoresis pattern. The pattern can then be compared with a standard gel pattern produced by separating, under the same or similar conditions, proteins isolated from normal or cancer cells. The standard gel pattern can be stored in, and retrieved from an electronic database of electrophoresis patterns. The presence or increased level of a Ub/proteasome pathway or ancillary protein marker in the two-dimensional gel provides an indication that the sample being tested was taken from a person with breast cancer. As with the other detection assays described herein, the detection of two or more proteins, for example, in the two-dimensional gel electrophoresis pattern further enhances the accuracy of the assay. The presence of a plurality, e.g., two to five, marker proteins on the two-dimensional gel provides an even stronger indication of the presence of a breast cancer in the individual. The assay thus permits the early detection and treatment of breast cancer.

The level of a Ub/proteasome pathway or ancillary marker protein can also be determined using any of a wide range of immunoassay techniques with qualitative or quantitative results. For example, the skilled artisan can employ the sandwich immunoassay format to detect breast cancer in a sample. Alternatively, the skilled artisan can use conventional immuno-histochemical procedures for detecting the presence of the Ub/proteasome pathway or ancillary protein in a sample using one or more labeled binding moieties. It is contemplated that either an absolute, semi-quantitative, or relative level of protein expression can be detected using the immunoassays disclosed herein.

In a sandwich immunoassay, two antibodies capable of binding the marker protein generally are used, e.g., one immobilized onto a solid support, and one free in solution and labeled with a detectable chemical compound. Examples of chemical labels that are useful for the second antibody include radioisotopes, fluorescent compounds, and enzymes or other molecules that generate colored or electrochemically active products when exposed to a reactant or enzyme substrate. When a sample containing the marker protein is placed in this system, the marker protein binds to both the immobilized antibody and the labeled antibody, to form a "sandwich" immune complex on the support's surface. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody or, for example, a hapten coupled thereto.

Both the sandwich immunoassay and tissue immunohistochemical procedures are highly specific and very sensitive, provided that labels with good limits of detection are used. A detailed review of immunological assay design, theory and protocols can be found in numerous texts in the art, including *Practical Immunology*, Butt, W. R., ed., (1984) Marcel Dekker, New York; and *Antibodies, A Laboratory Approach*, Harlow, et al., eds. (1988) Cold Spring Harbor Laboratory.

In general, immunoassay design considerations include preparation of antibodies (e.g., monoclonal or polyclonal antibodies), antibody fragments, or antibody derivatives having sufficiently high binding specificity for the target protein to form a complex that can be distinguished reliably from products of nonspecific interactions. As used herein, the term "antibody" is understood to mean binding proteins, for example, antibodies or other proteins containing an immunoglobulin variable region-like binding domain, having the appropriate binding affinities and specificities for the target protein. The higher the antibody binding specificity, the lower the target protein concentration that can be detected. As used herein, the terms "specific binding" or "specifically binds" are understood to mean that the binding moiety, for example, an antibody, has a binding affinity for the target protein of greater than $10^5$ $M^{-1}$ or greater than about $10^7$ $M^{-1}$.

Antibodies to Ub/proteasome pathway and ancillary protein markers which are useful in assays of the invention can be purchased from commercial sources (e.g., ABCAM, Cambridge, Mass.; Affiniti Inc., Exeter, UK; Boston Biochem, Cambridge, Mass.; and SIGMA, St. Louis Mo.) or generated using standard immunological procedures well-known and described in the art. See, for example, *Practical Immunology*, Butt, N. R., ed., (1984) supra. Briefly, an isolated target protein, e.g., having an amino acid sequence disclosed in a GEN-BANK Accession No. disclosed herein, is used to raise antibodies in a xenogeneic host, such as a mouse, goat or other suitable mammal. The marker protein is combined with a suitable adjuvant capable of enhancing antibody production in the host, and is injected into the host, for example, by intraperitoneal administration. Any adjuvant suitable for stimulating the host's immune response can be used. A commonly used adjuvant is Freund's complete adjuvant (an emulsion containing killed and dried microbial cells and available from, for example, CALBIOCHEM Corp. (San Diego, Calif.) or GIBCO-BRL (Grand Island, N.Y.). Where multiple antigen injections are desired, the subsequent injections can contain the antigen in combination with an incomplete adjuvant (e.g., cell-free emulsion). Polyclonal antibodies can be isolated from the antibody-producing host by extracting serum containing antibodies to the protein of interest. Monoclonal antibodies can be produced by isolating host cells that produce the desired antibody, fusing these cells with myeloma cells using standard procedures known in the immunology art, and screening for hybrid cells (hybridomas) that react specifically with the target protein and have the desired binding affinity.

Antibody binding domains also can be produced biosynthetically and the amino acid sequence of the binding domain manipulated to enhance binding affinity with a preferred epitope on the target protein. Specific antibody methodologies are well-understood and described in the literature. A more detailed description of their preparation can be found, for example, in *Practical Immunology* (1984) supra.

Chimeric antibodies are also contemplated. Techniques developed for the production of chimeric antibodies (Morrison, et al. (1984) *Proc. Natl. Acad. Sci. USA* 81:6851-6855; Neuberger, et al. (1984) *Nature* 312:604-608; Takeda, et al. (1985) *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region.

Antibodies can also be modified, e.g., to produce a number of well-characterized fragments generated by digestion with various peptidases. For example, pepsin digestion of an antibody produces F(ab)'$_2$. The F(ab)'$_2$ can further be reduced under mild conditions to break the disulfide linkage in the hinge region, thereby converting the F(ab)'$_2$ dimer into an Fab' monomer. The Fab' monomer is essentially a Fab with part of the hinge region (see, Fundamental Immunology, Third Edition (1993) W. E. Paul, ed., Raven Press, NY). While various antibody fragments are defined in terms of the digestion of an intact antibody, one of skill will appreciate that such fragments can be synthesized de novo either chemically or by utilizing recombinant DNA methodology. Accordingly, the term antibody fragment also includes fragments either produced by the modification of whole antibodies or those synthesized de novo using recombinant DNA methodologies. Thus, an antibody fragment includes, but is not limited to, single chain antibodies, Fab fragments, F(ab')$_2$ fragments, diabodies (Holliger, et al. (1993) *Proc. Natl. Acad. Sci. USA* 90:6444; Poljak (1994) *Structure* 2:1121-1123), fragments produced by a Fab expression library (Huse, et al. (1989) *Science* 246:1275-1281), and epitope-binding fragments of any of the above.

Antibody derivatives such as peptide aptamers, which are selected for specifically binding to an Ub/proteasome or ancillary protein in breast tissue or cells, are also provided in the instant invention. Peptide aptamers can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

While some embodiments embrace determining the level of Ub/proteasome pathway or ancillary protein, other embodiments embrace determining the activity of such proteins. As exemplified herein, an increase in Ub/proteasome pathway proteins is correlated with an increase in proteasome activity. Accordingly, proteasome activity, e.g., as determined using a fluorogenic substrate such as SUC-LLVY-AMC or detection of multiubiquinated proteins, can also be used for diagnosing and monitoring breast cancer in an individual.

Binding moieties to the instant protein markers are used in the assays disclosed herein as well as in kits to determine the level of the proteins in a sample. For example, a kit of the invention can include one or more binding moieties (e.g., antibodies, antibody fragments, or antibody derivatives) which bind specifically to one or more Ub/proteasome pathway or ancillary proteins and which permit the relative level and/or specific concentration of the Ub/proteasome pathway or ancillary proteins to be detected and/or quantitated in a sample.

Suitable kits for detecting Ub/proteasome pathway or ancillary proteins are contemplated to include, e.g., a receptacle or other means for capturing a sample to be evaluated, and means for determining the presence and/or quantity in the sample of one or more of the Ub/proteasome pathway or ancillary proteins described herein. As used herein, "means for determining" in one embodiment includes one or more antibodies specific for these proteins and means for detecting the binding of the antibodies to these proteins by, e.g., a standard sandwich immunoassay as described herein. Where the presence of a protein within a cell is to be detected, e.g., as from a sample, the kit also can include a means for disrupting the cell structure so as to expose intracellular proteins. The kit can further contain written information, such as procedures for carrying out the method of the present invention or analytical information, such as representative images of breast cancer tumor samples with low or high levels of marker protein expression as compared to a control.

In other embodiments of the present invention, the presence of breast cancer in an individual also can be determined by detecting, in a sample, one or more nucleic acid molecules encoding one or more Ub/proteasome pathway or ancillary proteins. Using methods well-known to those of ordinary skill in the art, one or more oligonucleotide probes are designed to specifically hybridize with a nucleic acid molecule encoding a Ub/proteasome pathway or ancillary protein, e.g., nucleic acid molecules disclosed in the GENBANK Accession Nos. disclosed herein.

A target nucleic acid molecule encoding an Ub/proteasome pathway or ancillary protein marker can be detected using a labeled binding moiety capable of specifically binding the target nucleic acid. The binding moiety can be, for example, a protein, a nucleic acid or a peptide nucleic acid. Additionally, a target nucleic acid, such as an mRNA encoding a Ub/proteasome pathway or ancillary protein, can be detected by conducting, for example, a northern blot analysis using labeled oligonucleotides, e.g., nucleic acid fragments complementary to and capable of hybridizing specifically with at least a portion of a target nucleic acid.

More specifically, gene probes composed of complementary RNA or, preferably, DNA to the Ub/proteasome pathway or ancillary protein nucleotide sequences or mRNA sequences encoding Ub/proteasome pathway or ancillary proteins can be produced using established recombinant techniques or oligonucleotide synthesis. The probes hybridize with complementary nucleic acid sequences presented in the test specimen, and provide exquisite specificity. A short, well-defined probe, coding for a single unique sequence is most precise and preferred. Larger probes are generally less specific. While an oligonucleotide of any length can hybridize to an mRNA transcript, oligonucleotides typically within the range of 8-100 nucleotides, preferably within the range of 15-50 nucleotides, are envisioned to be most useful in standard hybridization assays. Choices of probe length and sequence allow one to choose the degree of specificity desired. Hybridization is generally carried out at from 50° C. to 65° C. in a high salt buffer solution, formamide or other agents to set the degree of complementarity required. Furthermore, the state of the art is such that probes can be manufactured to recognize essentially any DNA or RNA sequence. For additional methodologies, see, for example, Guide to Molecular Techniques, Berger, et al. (1987) Methods of Enzymology, Vol. 152.

A wide variety of different labels coupled to the probes or antibodies can be employed in the instant assays. The labeled reagents can be provided in solution or coupled to an insoluble support, depending on the design of the assay. The various conjugates can be joined covalently or noncovalently, directly or indirectly. When bonded covalently, the particular linkage group will depend upon the nature of the two moieties to be bonded. A large number of linking groups and methods for linking are taught in the literature. Broadly, the labels can be divided into the following categories: chromogens; catalyzed reactions; chemiluminescence; radioactive labels; and colloidal-sized colored particles. The chromogens include compounds which absorb light in a distinctive range so that a color is observed, or emit light when irradiated with light of a particular wavelength or wavelength range, e.g., fluorescers. Both enzymatic and nonenzymatic catalysts can be employed. In choosing an enzyme, there will be many considerations including the stability of the enzyme, whether it is normally present in samples of the type for which the assay is designed, the nature of the substrate, and the effect if any of conjugation on the enzyme's properties. Useful enzyme labels include oxiodoreductases, transferases, hydrolases, lyases, isomerases, ligases, or synthetases. A chemiluminescent label involves a compound that becomes electronically excited by a chemical reaction and emits light that serves as a detectable signal or donates energy to a fluorescent acceptor. Radioactive labels include various radioisotopes found in common use such as the unstable forms of hydrogen, iodine, phosphorus or the like. Colloidal-sized colored particles involve material such as colloidal gold that, in aggregate, form a visually detectable distinctive spot corresponding to the site of a substance to be detected. Additional information on labeling technology is disclosed, for example, in U.S. Pat. No. 4,366,241.

A common method of in vitro labeling of nucleotide probes involves nick translation, wherein the unlabeled DNA probe is nicked with an endonuclease to produce free 3'-hydroxyl termini within either strand of the double-stranded fragment. Simultaneously, an exonuclease removes the nucleotide residue from the 5' phosphoryl side of the nick. The sequence of replacement nucleotides is determined by the sequence of the opposite strand of the duplex. Thus, if labeled nucleotides are supplied, DNA polymerase will fill in the nick with the labeled nucleotides. Using this well-known technique, up to 50% of the molecule can be labeled. For smaller probes, known methods involving 3'-end labeling can be used. Furthermore, there are commercially available methods of labeling DNA with fluorescent molecules, catalysts, enzymes, or chemiluminescent materials. Biotin labeling kits are commercially available (ENZO Biochem Inc.) under the trademark BIO-PROBE. This type of system permits the probe to be coupled to avidin which in turn is labeled with, for example, a fluorescent molecule, enzyme, antibody, etc. For further disclosure regarding probe construction and technology, see, for example, Sambrook et al. (1982) *Molecular Cloning, A Laboratory Manual* (Cold Spring Harbor, N.Y.).

The oligonucleotide selected for hybridizing to the target nucleic acid, whether synthesized chemically or by recombinant DNA methodologies, is isolated and purified using standard techniques and then preferably labeled (e.g., with $^{35}$S or $^{32}$P) using standard labeling protocols. A sample containing the target nucleic acid then is separated in an electrophoresis gel, the dispersed nucleic acids transferred to a nitrocellulose filter and the labeled oligonucleotide exposed to the filter under stringent hybridization conditions, e.g., 50% formamide, 5×SSPE, 2×Denhardt's solution, 0.1% SDS at 42° C., as described in Sambrook et al. (1989) supra. The filter can then be washed using 2×SSPE, 0.1% SDS at 68° C., and more preferably using 0.1×SSPE, 0.1% SDS at 68° C. Other useful procedures known in the art include solution hybridization, and dot and slot RNA hybridization. Optionally, the amount of the target nucleic acid present in a sample is then quantitated by measuring the radioactivity of hybridized fragments, using standard procedures known in the art.

Alternatively, combinations of appropriate oligonucleotide primers, i.e., more than one primer, are used to determine the level of expression of a target gene by standard polymerase chain reaction (PCR) procedures, for example, by quantitative PCR. Conventional PCR-based assays are discussed, for example, in Innes, et al. (1990) *PCR Protocols; A guide to methods and Applications*, Academic Press; and Innes, et al. (1995) *PCR Strategies*, Academic Press, San Diego, Calif.

Once the level or activity of Ub/proteasome pathway or ancillary protein or nucleic acid encoding such protein is determined or measured in the test sample, it is compared to the level or activity of Ub/proteasome pathway or ancillary protein or nucleic acid encoding such protein in one or more controls in order to determine whether the subject from which the sample was obtained has breast cancer. As exemplified herein, a control can be a sample obtained from healthy breast tissue of the subject being tested or can be a representative normal or breast tissue sample with normal levels of Ub/proteasome pathway or ancillary protein expression or activity. By using one or more control samples (e.g., in a panel), the skilled pathologist can compare the intensity of staining of the Ub/proteasome pathway or ancillary protein in an immunohistochemical assay or absolute level of expression in an ELISA for a semi-quantitative or quantitative, respectively, determination of Ub/proteasome pathway or ancillary protein levels in a test sample from a subject. Moreover, in particular embodiments, the instant method is employed for distinguishing between benign and malignant tumor cells.

Using the instant assay, progression of the breast cancer or the therapeutic efficacy of chemotherapy can be measured. For example, the level of one or more Ub/proteasome pathway or ancillary protein in breast cancer cells is compared to standards from healthy, untreated tissue the start of therapy. Samples are collected at discrete intervals during treatment and also compared to the standard. Changes in the level of the marker protein(s), for example, will be indicative of the efficacy of treatment (that is, the rate of cancer cell death). Moreover, the instant marker proteins can be used to monitor recurrence of breast cancer. For example, samples are collected at periodic intervals (e.g., every month, 6 months or year) after chemotherapy, radiation therapy or mastectomy, and the level of one or more Ub/proteasome pathway or ancillary protein in the samples is determined and compared to a standard or control to monitor recurrence of breast cancer.

Using the instant marker proteins, it is contemplated that a variety of therapies can also be developed for treating breast cancer. Because the marker proteins described herein are present at detectably higher levels in breast cancer cells relative to normal breast cells, the skilled artisan may employ, for example, the marker proteins and/or nucleic acids encoding the marker proteins as target molecules for a cancer chemotherapy.

The invention is described in greater detail by the following non-limiting examples.

EXAMPLE 1

Materials

All tissue samples (breast and colon cancer) were purchased from the Cancer Institute of New Jersey Tissue Retrieval Service (New Brunswick, N.J.). Specimens were obtained in pairs, which represented previously diagnosed breast/colon cancer and patient-matched normal adjacent tissue. A pathology report accompanied each specimen and provided a characterization of the sample. Two benign tumor samples were also obtained, although only one included a patient-matched control specimen. Benign tumor samples were typically not archived; therefore, only limited samples were available.

The UbL domains from human hHR23A (1-79) and hHR23B (1-78), as well as yeast Rad23 (1-77) and Dsk2 (1-76) were cloned into pCBGST1 (Schauber, et al. (1998) *Nature* 391:715-8). Similar constructs for expression in *E. coli* were generated in pGEX-2TK (Amersham-Bioscience, Piscataway, N.J.). Amino acid substitution mutations in the UbL domains were generated by PCR, and confirmed by DNA sequencing (IDT Integrated Technologies, Coralville, Iowa).

EXAMPLE 2

Preparation of Protein and Tissue Extracts

Each tissue sample was suspended in 2 mL lysis buffer (50 mmol/L HEPES (pH 7.5), 150 mmol/L NaCl, 5 mmol/L Na-EDTA) that contained protease inhibitors (Roche, Indianapolis, Ind.). Proteasome inhibitors were not added to these tissue extracts. Tissues were kept on ice and disrupted using a tissue homogenizer (POLYTRON® PT 3100; Brinkman Instruments, Westbury, N.Y.) using brief pulses, for a total of 30 to 45 seconds. Lysates were further diluted into 2 mL lysis buffer containing 1% TRITON™ X-100, and then centrifuged at 12,000×g for 20 minutes at 4° C. Protein concentration was determined using the Bradford reagent (BIO-RAD®, Bethesda, Md.).

GST-UbL fusion proteins were purified from yeast, and extracts prepared using established methods (Schauber, et al. (1998) supra). Equal amount of protein was applied to glutathione-SEPHAROSE™ beads, and the bound proteins were released in SDS-containing sample buffer and resolved in SDS-polyacrylamide gels. The separated proteins were transferred to nitrocellulose, and the filter stained with Ponceau S prior to immunoblot analysis. Expression and purification of GST-fusion proteins from E. coli was according to standard methods.

Cultured mammalian cells were grown in appropriate medium at 37° C. with 5% $CO_2$ and were collected at 90% confluence. Cell pellets and human tissue specimens were suspended in buffer, lysed by sonication, and cell debris removed by brief centrifugation.

EXAMPLE 3

Antibodies and Immunoblot Analysis

Antibodies against Rpt1, Rpn2, and 20S core α-subunits, were purchased from Affiniti, Inc. (Exeter, United Kingdom). Antibodies against Ub-conjugating enzymes were from Boston Biochem (Cambridge, Mass.), and Ub antibody was purchased from SIGMA (St. Louis, Mo.). Antibodies against eEF1A were obtained from Upstate USA (Charlottesville, Va.) and vimentin antibodies were obtained from Lab Vision Corp. (Fremont, Calif.). Equal amounts of protein extract (30 µg) were resolved in 10% SDS-polyacrylamide gels (SDS-PAGE), and transferred to nitrocellulose (HOEFER® TE70-Semi-Dry; GE Healthcare, Piscataway, N.J.). The filters were sequentially incubated with antibodies against Rpt1, UbcH5, and Ub. Due to the high-level expression of eEF1A, 10 µg of the same protein preparations were resolved in a separate polyacrylamide gel. The reactions were detected with enhanced chemiluminescence (NEN/PERKIN-ELMER, Boston, Mass.) and quantified using KODAK® 1D densitometry software (KODAK, Rochester, N.Y.).

EXAMPLE 4

Proteasome Activity Determination

Equal amount of lysate was mixed with 1 mL proteasome assay buffer (25 mmol/L HEPES (pH 7.5), 0.5 mmol/L EDTA), containing 40 µmol/L fluorogenic substrate SUC-LLVY-AMC (Boston Biochem) and the hydrolysis was determined following a 3-hour incubation at 37° C. The fluorescence measurements represented chymotrypsin-like activity, and were determined using a Turner 7000 fluorometer. The assays were conducted in duplicate and the average value was obtained. All the values were adjusted to their respective control (normal adjacent tissue, NAT) specimens, which was set to an arbitrary value of 100.

EXAMPLE 5

Mass Spectrometry

Polyacrylamide gels were stained with COOMASSIE blue and proteins bands were excised and identified by mass spectrometry at the Center for Advanced Proteomics Research-New Jersey Medical School (New Brunswick, N.J.).

What is claimed is:

1. A kit comprising
(a) an antibody-based binding moiety that specifically binds UbcH5 or Ubc4; and
(b) an antibody-based binding moiety that specifically binds to a PA28 protein or a subunit thereof.

* * * * *

SEQUENCE LISTING

```
<160> NUMBER OF SEQ ID NOS: 13

<210> SEQ ID NO 1
<211> LENGTH: 80
<212> TYPE: PRT
<213> ORGANISM: Homo sapiens

<400> SEQUENCE: 1

Met Ala Val Thr Ile Thr Leu Lys Thr Leu Gln Gln Gln Thr Phe Lys
1               5                   10                  15

Ile Arg Met Glu Pro Asp Glu Thr Val Lys Val Leu Lys Glu Lys Ile
            20                  25                  30

Glu Ala Glu Lys Gly Arg Asp Ala Phe Pro Val Ala Gly Gln Lys Leu
        35                  40                  45

Ile Tyr Ala Gly Lys Ile Leu Ser Asp Asp Val Pro Ile Arg Asp Tyr
    50                  55                  60

Arg Ile Asp Glu Lys Asn Phe Val Val Val Met Val Thr Lys Thr Lys
65                  70                  75                  80
```

```
<210> SEQ ID NO 2
<211> LENGTH: 78
<212> TYPE: PRT
<213> ORGANISM: Homo sapiens

<400> SEQUENCE: 2

Met Gln Val Thr Leu Lys Thr Leu Gln Gln Thr Phe Lys Ile Asp
1               5                   10                  15

Ile Asp Pro Glu Glu Thr Val Lys Ala Leu Lys Glu Lys Ile Glu Ser
                20                  25                  30

Glu Lys Gly Lys Asp Ala Phe Pro Val Ala Gly Gln Lys Leu Ile Tyr
            35                  40                  45

Ala Gly Lys Ile Leu Asn Asp Asp Thr Ala Leu Lys Glu Tyr Lys Ile
        50                  55                  60

Asp Glu Lys Asn Phe Val Val Val Met Val Thr Lys Pro Lys
65                  70                  75

<210> SEQ ID NO 3
<211> LENGTH: 79
<212> TYPE: PRT
<213> ORGANISM: Saccharomyces cerevisiae

<400> SEQUENCE: 3

Met Val Ser Leu Thr Phe Lys Asn Phe Lys Lys Glu Lys Val Pro Leu
1               5                   10                  15

Asp Leu Glu Pro Ser Asn Thr Ile Leu Glu Thr Lys Thr Lys Leu Ala
                20                  25                  30

Gln Ser Ile Ser Cys Glu Glu Ser Gln Ile Lys Leu Ile Tyr Ser Gly
            35                  40                  45

Lys Val Leu Gln Asp Ser Lys Thr Val Ser Glu Cys Gly Leu Lys Asp
        50                  55                  60

Gly Asp Gln Val Val Phe Met Val Ser Gln Lys Lys Ser Thr Lys
65                  70                  75

<210> SEQ ID NO 4
<211> LENGTH: 80
<212> TYPE: PRT
<213> ORGANISM: Saccharomyces cerevisiae

<400> SEQUENCE: 4

Met Ser Leu Asn Ile His Ile Lys Ser Gly Gln Asp Lys Trp Glu Val
1               5                   10                  15

Asn Val Ala Pro Glu Ser Thr Val Leu Gln Phe Lys Glu Ala Ile Asn
                20                  25                  30

Lys Ala Asn Gly Ile Pro Val Ala Asn Gln Arg Leu Ile Tyr Ser Gly
            35                  40                  45

Lys Ile Leu Lys Asp Asp Gln Thr Val Glu Ser Tyr His Ile Gln Asp
        50                  55                  60

Gly His Ser Val His Leu Val Lys Ser Gln Pro Lys Pro Gln Thr Ala
65                  70                  75                  80

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Val Val Val Met Val Thr Lys Thr
```

-continued

```
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Val Val Val Met Val Thr Lys Pro Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Val Val Val Met Val Thr Lys
1               5

<210> SEQ ID NO 8
<211> LENGTH: 433
<212> TYPE: PRT
<213> ORGANISM: Homo sapiens

<400> SEQUENCE: 8

Met Pro Asp Tyr Leu Gly Ala Asp Gln Arg Lys Thr Lys Glu Asp Glu
1               5                   10                  15

Lys Asp Asp Lys Pro Ile Arg Ala Leu Asp Glu Gly Asp Ile Ala Leu
                20                  25                  30

Leu Lys Thr Tyr Gly Gln Ser Thr Tyr Ser Arg Gln Ile Lys Gln Val
            35                  40                  45

Glu Asp Asp Ile Gln Gln Leu Leu Lys Lys Ile Asn Glu Leu Thr Gly
        50                  55                  60

Ile Lys Glu Ser Asp Thr Gly Leu Ala Pro Pro Ala Leu Trp Asp Leu
65                  70                  75                  80

Ala Ala Asp Lys Gln Thr Leu Gln Ser Glu Gln Pro Leu Gln Val Ala
                85                  90                  95

Arg Cys Thr Lys Ile Ile Asn Ala Asp Ser Glu Asp Pro Lys Tyr Ile
                100                 105                 110

Ile Asn Val Lys Gln Phe Ala Lys Phe Val Val Asp Leu Ser Asp Gln
            115                 120                 125

Val Ala Pro Thr Asp Ile Glu Glu Gly Met Arg Val Gly Val Asp Arg
        130                 135                 140

Asn Lys Tyr Gln Ile His Ile Pro Leu Pro Pro Lys Ile Asp Pro Thr
145                 150                 155                 160

Val Thr Met Met Gln Val Glu Glu Lys Pro Asp Val Thr Tyr Ser Asp
                165                 170                 175

Val Gly Gly Cys Lys Glu Gln Ile Glu Lys Leu Arg Glu Val Val Glu
                180                 185                 190

Thr Pro Leu Leu His Pro Glu Arg Phe Val Asn Leu Gly Ile Glu Pro
            195                 200                 205

Pro Lys Gly Val Leu Leu Phe Gly Pro Pro Gly Thr Gly Lys Thr Leu
        210                 215                 220

Cys Ala Arg Ala Val Ala Asn Arg Thr Asp Ala Cys Phe Ile Arg Val
```

```
            225                 230                 235                 240

Ile Gly Ser Glu Leu Val Gln Lys Tyr Val Gly Glu Gly Ala Arg Met
                    245                 250                 255

Val Arg Glu Leu Phe Glu Met Ala Arg Thr Lys Lys Ala Cys Leu Ile
                    260                 265                 270

Phe Phe Asp Glu Ile Asp Ala Ile Gly Gly Ala Arg Phe Asp Asp Gly
                    275                 280                 285

Ala Gly Gly Asp Asn Glu Val Gln Arg Thr Met Leu Glu Leu Ile Asn
                    290                 295                 300

Gln Leu Asp Gly Phe Asp Pro Arg Gly Asn Ile Lys Val Leu Met Ala
    305                 310                 315                 320

Thr Asn Arg Pro Asp Thr Leu Asp Pro Ala Leu Met Arg Pro Gly Arg
                    325                 330                 335

Leu Asp Arg Lys Ile Glu Phe Ser Leu Pro Asp Leu Glu Gly Arg Thr
                    340                 345                 350

His Ile Phe Lys Ile His Ala Arg Ser Met Ser Val Glu Arg Asp Ile
                    355                 360                 365

Arg Phe Glu Leu Leu Ala Arg Leu Cys Pro Asn Ser Thr Gly Ala Glu
                    370                 375                 380

Ile Arg Ser Val Cys Thr Glu Ala Gly Met Phe Ala Ile Arg Ala Arg
    385                 390                 395                 400

Arg Lys Ile Ala Thr Glu Lys Asp Phe Leu Glu Ala Val Asn Lys Val
                    405                 410                 415

Ile Lys Ser Tyr Ala Lys Phe Ser Ala Thr Pro Arg Tyr Met Thr Tyr
                    420                 425                 430

Asn

<210> SEQ ID NO 9
<211> LENGTH: 953
<212> TYPE: PRT
<213> ORGANISM: Homo sapiens

<400> SEQUENCE: 9

Met Ile Thr Ser Ala Ala Gly Ile Ile Ser Leu Leu Asp Glu Asp Glu
    1               5                   10                  15

Pro Gln Leu Lys Glu Phe Ala Leu His Lys Leu Asn Ala Val Val Asn
                    20                  25                  30

Asp Phe Trp Ala Glu Ile Ser Glu Ser Val Asp Lys Ile Glu Val Leu
                    35                  40                  45

Tyr Glu Asp Glu Gly Phe Arg Ser Arg Gln Phe Ala Ala Leu Val Ala
    50                  55                  60

Ser Lys Val Phe Tyr His Leu Gly Ala Phe Glu Glu Ser Leu Asn Tyr
    65                  70                  75                  80

Ala Leu Gly Ala Gly Asp Leu Phe Asn Val Asn Asp Asn Ser Glu Tyr
                    85                  90                  95

Val Glu Thr Ile Ile Ala Lys Cys Ile Asp His Tyr Thr Lys Gln Cys
                    100                 105                 110

Val Glu Asn Ala Asp Leu Pro Glu Gly Glu Lys Lys Pro Ile Asp Gln
                    115                 120                 125

Arg Leu Glu Gly Ile Val Asn Lys Met Phe Gln Arg Cys Leu Asp Asp
                    130                 135                 140

His Lys Tyr Lys Gln Ala Ile Gly Ile Ala Leu Glu Thr Arg Arg Leu
    145                 150                 155                 160

Asp Val Phe Glu Lys Thr Ile Leu Glu Ser Asn Asp Val Pro Gly Met
```

-continued

```
            165                 170                 175
Leu Ala Tyr Ser Leu Lys Leu Cys Met Ser Leu Met Gln Asn Lys Gln
            180                 185                 190

Phe Arg Asn Lys Val Leu Arg Val Val Lys Ile Tyr Met Asn Leu
            195                 200                 205

Glu Lys Pro Asp Phe Ile Asn Val Cys Gln Cys Leu Ile Phe Leu Asp
            210                 215                 220

Asp Pro Gln Ala Val Ser Asp Ile Leu Glu Lys Leu Val Lys Glu Asp
225                 230                 235                 240

Asn Leu Leu Met Ala Tyr Gln Ile Cys Phe Asp Leu Tyr Glu Ser Ala
                    245                 250                 255

Ser Gln Gln Phe Leu Ser Ser Val Ile Gln Asn Leu Arg Thr Val Gly
                260                 265                 270

Thr Pro Ile Ala Ser Val Pro Gly Ser Thr Asn Thr Gly Thr Val Pro
            275                 280                 285

Gly Ser Glu Lys Asp Ser Asp Ser Met Glu Thr Glu Glu Lys Thr Ser
            290                 295                 300

Ser Ala Phe Val Gly Lys Thr Pro Glu Ala Ser Pro Glu Pro Lys Asp
305                 310                 315                 320

Gln Thr Leu Lys Met Ile Lys Ile Leu Ser Gly Glu Met Ala Ile Glu
                    325                 330                 335

Leu His Leu Gln Phe Leu Ile Arg Asn Asn Thr Asp Leu Met Ile
                340                 345                 350

Leu Lys Asn Thr Lys Asp Ala Val Arg Asn Ser Val Cys His Thr Ala
                355                 360                 365

Thr Val Ile Ala Asn Ser Phe Met His Cys Gly Thr Thr Ser Asp Gln
            370                 375                 380

Phe Leu Arg Asp Asn Leu Glu Trp Leu Ala Arg Ala Thr Asn Trp Ala
385                 390                 395                 400

Lys Phe Thr Ala Thr Ala Ser Leu Gly Val Ile His Lys Gly His Glu
                    405                 410                 415

Lys Glu Ala Leu Gln Leu Met Ala Thr Tyr Leu Pro Lys Asp Thr Ser
                420                 425                 430

Pro Gly Ser Ala Tyr Gln Glu Gly Gly Leu Tyr Ala Leu Gly Leu
            435                 440                 445

Ile His Ala Asn His Gly Gly Asp Ile Ile Asp Tyr Leu Leu Asn Gln
            450                 455                 460

Leu Lys Asn Ala Ser Asn Asp Ile Val Arg His Gly Gly Ser Leu Gly
465                 470                 475                 480

Leu Gly Leu Ala Ala Met Gly Thr Ala Arg Gln Asp Val Tyr Asp Leu
                    485                 490                 495

Leu Lys Thr Asn Leu Tyr Gln Asp Ala Val Thr Gly Glu Ala Ala
                500                 505                 510

Gly Leu Ala Leu Gly Leu Val Met Leu Gly Ser Lys Asn Ala Gln Ala
                515                 520                 525

Ile Glu Asp Met Val Gly Tyr Ala Gln Glu Thr Gln His Glu Lys Ile
            530                 535                 540

Leu Arg Gly Leu Ala Val Gly Ile Ala Leu Val Met Tyr Gly Arg Met
545                 550                 555                 560

Glu Glu Ala Asp Ala Leu Ile Glu Ser Leu Cys Arg Asp Lys Asp Pro
                    565                 570                 575

Ile Leu Arg Arg Ser Gly Met Tyr Thr Val Ala Met Ala Tyr Cys Gly
                580                 585                 590
```

Ser Gly Asn Asn Lys Ala Ile Arg Arg Leu Leu His Val Ala Val Ser
        595                 600                 605

Asp Val Asn Asp Asp Val Arg Arg Ala Ala Val Glu Ser Leu Gly Phe
610                 615                 620

Ile Leu Phe Arg Thr Pro Glu Gln Cys Pro Ser Val Val Ser Leu Leu
625                 630                 635                 640

Ser Glu Ser Tyr Asn Pro His Val Arg Tyr Gly Ala Ala Met Ala Leu
            645                 650                 655

Gly Ile Cys Cys Ala Gly Thr Gly Asn Lys Glu Ala Ile Asn Leu Leu
            660                 665                 670

Glu Pro Met Thr Asn Asp Pro Val Asn Tyr Val Arg Gln Gly Ala Leu
        675                 680                 685

Ile Ala Ser Ala Leu Ile Met Ile Gln Gln Thr Glu Ile Thr Cys Pro
690                 695                 700

Lys Val Asn Gln Phe Arg Gln Leu Tyr Ser Lys Val Ile Asn Asp Lys
705                 710                 715                 720

His Asp Asp Val Met Ala Lys Phe Gly Ala Ile Leu Ala Gln Gly Ile
                725                 730                 735

Leu Asp Ala Gly Gly His Asn Val Thr Ile Ser Leu Gln Ser Arg Thr
            740                 745                 750

Gly His Thr His Met Pro Ser Val Val Gly Val Leu Val Phe Thr Gln
        755                 760                 765

Phe Trp Phe Trp Phe Pro Leu Ser His Phe Leu Ser Leu Ala Tyr Thr
770                 775                 780

Pro Thr Cys Val Ile Gly Leu Asn Lys Asp Leu Lys Met Pro Lys Val
785                 790                 795                 800

Gln Tyr Lys Ser Asn Cys Lys Pro Ser Thr Phe Ala Tyr Pro Ala Pro
                805                 810                 815

Leu Glu Val Pro Lys Glu Lys Glu Lys Val Ser Thr Ala Val
            820                 825                 830

Leu Ser Ile Thr Ala Lys Ala Lys Lys Glu Lys Glu Lys
        835                 840                 845

Lys Glu Glu Glu Lys Met Glu Val Asp Glu Ala Glu Lys Lys Glu Glu
        850                 855                 860

Lys Glu Lys Lys Lys Glu Pro Glu Pro Asn Phe Gln Leu Leu Asp Asn
865                 870                 875                 880

Pro Ala Arg Val Met Pro Ala Gln Leu Lys Val Leu Thr Met Pro Glu
                885                 890                 895

Thr Cys Arg Tyr Gln Pro Phe Lys Pro Leu Ser Ile Gly Gly Ile Ile
                900                 905                 910

Ile Leu Lys Asp Thr Ser Glu Asp Ile Glu Glu Leu Val Glu Pro Val
            915                 920                 925

Ala Ala His Gly Pro Lys Ile Glu Glu Glu Gln Glu Pro Glu Pro
            930                 935                 940

Pro Glu Pro Phe Glu Tyr Ile Asp Asp
945                 950

<210> SEQ ID NO 10
<211> LENGTH: 183
<212> TYPE: PRT
<213> ORGANISM: Homo sapiens

<400> SEQUENCE: 10

Met Ser Ser Pro Ser Pro Gly Lys Arg Arg Met Asp Thr Asp Val Val

-continued

```
               1               5                  10                 15
            Lys Leu Ile Glu Ser Lys His Glu Val Thr Ile Leu Gly Gly Leu Asn
                            20                 25                 30

Glu Phe Val Val Lys Phe Tyr Gly Pro Gln Gly Thr Pro Tyr Glu Gly
                            35                 40                 45

Gly Val Trp Lys Val Arg Val Asp Leu Pro Asp Lys Tyr Pro Phe Lys
             50                            55                 60

Ser Pro Ser Ile Gly Phe Met Asn Lys Ile Phe His Pro Asn Ile Asp
             65                            70                 75                 80

Glu Ala Ser Gly Thr Val Cys Leu Asp Val Ile Asn Gln Thr Trp Thr
                                       85                 90                 95

Ala Leu Tyr Asp Leu Thr Asn Ile Phe Glu Ser Phe Leu Pro Gln Leu
                           100                105                110

Leu Ala Tyr Pro Asn Pro Ile Asp Pro Leu Asn Gly Asp Ala Ala Ala
                           115                120                125

Met Tyr Leu His Arg Pro Glu Glu Tyr Lys Gln Lys Ile Lys Glu Tyr
                           130                135                140

Ile Gln Lys Tyr Ala Thr Glu Glu Ala Leu Lys Glu Gln Glu Glu Gly
            145                           150                155                160

Thr Gly Asp Ser Ser Glu Ser Ser Met Ser Asp Phe Ser Glu Asp
                                          165                170                175

Glu Ala Gln Asp Met Glu Leu
                           180
```

<210> SEQ ID NO 11
<211> LENGTH: 147
<212> TYPE: PRT
<213> ORGANISM: Homo sapiens

<400> SEQUENCE: 11

```
            Met Ala Leu Lys Arg Ile Gln Lys Glu Leu Ser Asp Leu Gln Arg Asp
             1               5                 10                 15

Pro Pro Ala His Cys Ser Ala Gly Pro Val Gly Asp Asp Leu Phe His
                            20                 25                 30

Trp Gln Ala Thr Ile Met Gly Pro Pro Asp Ser Ala Tyr Gln Gly Gly
                            35                 40                 45

Val Phe Phe Leu Thr Val His Phe Pro Thr Asp Tyr Pro Phe Lys Pro
             50                            55                 60

Pro Lys Ile Ala Phe Thr Thr Lys Ile Tyr His Pro Asn Ile Asn Ser
             65                            70                 75                 80

Asn Gly Ser Ile Cys Leu Asp Ile Leu Arg Ser Gln Trp Ser Pro Ala
                                       85                 90                 95

Leu Thr Val Ser Lys Val Leu Leu Ser Ile Cys Ser Leu Leu Cys Asp
                           100                105                110

Pro Asn Pro Asp Asp Pro Leu Val Pro Asp Ile Ala Gln Ile Tyr Lys
                           115                120                125

Ser Asp Lys Glu Lys Tyr Asn Arg His Ala Arg Glu Trp Thr Gln Lys
                           130                135                140

Tyr Ala Met
            145
```

<210> SEQ ID NO 12
<211> LENGTH: 200
<212> TYPE: PRT
<213> ORGANISM: Homo sapiens

```
<400> SEQUENCE: 12

Met Ala Asn Ile Ala Val Gln Arg Ile Lys Arg Glu Phe Lys Glu Val
1               5                   10                  15

Leu Lys Ser Glu Glu Thr Ser Lys Asn Gln Ile Lys Val Asp Leu Val
            20                  25                  30

Asp Glu Asn Phe Thr Glu Leu Arg Gly Glu Ile Ala Gly Pro Pro Asp
                35                  40                  45

Thr Pro Tyr Glu Gly Gly Arg Tyr Gln Leu Glu Ile Lys Ile Pro Glu
    50                  55                  60

Thr Tyr Pro Phe Asn Pro Pro Lys Val Arg Phe Ile Thr Lys Ile Trp
65                  70                  75                  80

His Pro Asn Ile Ser Ser Val Thr Gly Ala Ile Cys Leu Asp Ile Leu
                85                  90                  95

Lys Asp Gln Trp Ala Ala Ala Met Thr Leu Arg Thr Val Leu Leu Ser
            100                 105                 110

Leu Gln Ala Leu Leu Ala Ala Ala Glu Pro Asp Asp Pro Gln Asp Ala
        115                 120                 125

Val Val Ala Asn Gln Tyr Lys Gln Asn Pro Glu Met Phe Lys Gln Thr
130                 135                 140

Ala Arg Leu Trp Ala His Val Tyr Ala Gly Ala Pro Val Ser Ser Pro
145                 150                 155                 160

Glu Tyr Thr Lys Lys Ile Glu Asn Leu Cys Ala Met Gly Phe Asp Arg
                165                 170                 175

Asn Ala Val Ile Val Ala Leu Ser Ser Lys Ser Trp Asp Val Glu Thr
            180                 185                 190

Ala Thr Glu Leu Leu Leu Ser Asn
        195                 200

<210> SEQ ID NO 13
<211> LENGTH: 462
<212> TYPE: PRT
<213> ORGANISM: Homo sapiens

<400> SEQUENCE: 13

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160
```

```
Pro Tyr Ser Gln Lys Arg Tyr Glu Glu Ile Val Lys Glu Val Ser Thr
            165                 170                 175
Tyr Ile Lys Lys Ile Gly Tyr Asn Pro Asp Thr Val Ala Phe Val Pro
            180                 185                 190
Ile Ser Gly Trp Asn Gly Asp Asn Met Leu Glu Pro Ser Ala Asn Met
            195                 200                 205
Pro Trp Phe Lys Gly Trp Lys Val Thr Arg Lys Asp Gly Asn Ala Ser
210             215                 220
Gly Thr Thr Leu Leu Glu Ala Leu Asp Cys Ile Leu Pro Pro Thr Arg
225                 230                 235                 240
Pro Thr Asp Lys Pro Leu Arg Leu Pro Leu Gln Asp Val Tyr Lys Ile
            245                 250                 255
Gly Gly Ile Gly Thr Val Pro Val Gly Arg Val Glu Thr Gly Val Leu
            260                 265                 270
Lys Pro Gly Met Val Val Thr Phe Ala Pro Val Asn Val Thr Thr Glu
            275                 280                 285
Val Lys Ser Val Glu Met His His Glu Ala Leu Ser Glu Ala Leu Pro
            290                 295                 300
Gly Asp Asn Val Gly Phe Asn Val Lys Asn Val Ser Val Lys Asp Val
305                 310                 315                 320
Arg Arg Gly Asn Val Ala Gly Asp Ser Lys Asn Asp Pro Pro Met Glu
                325                 330                 335
Ala Ala Gly Phe Thr Ala Gln Val Ile Ile Leu Asn His Pro Gly Gln
                340                 345                 350
Ile Ser Ala Gly Tyr Ala Pro Val Leu Asp Cys His Thr Ala His Ile
            355                 360                 365
Ala Cys Lys Phe Ala Glu Leu Lys Glu Lys Ile Asp Arg Arg Ser Gly
            370                 375                 380
Lys Lys Leu Glu Asp Gly Pro Lys Phe Leu Lys Ser Gly Asp Ala Ala
385                 390                 395                 400
Ile Val Asp Met Val Pro Gly Lys Pro Met Cys Val Glu Ser Phe Ser
                405                 410                 415
Asp Tyr Pro Pro Leu Gly Arg Phe Ala Val Arg Asp Met Arg Gln Thr
            420                 425                 430
Val Ala Val Gly Val Ile Lys Ala Val Asp Lys Lys Ala Ala Gly Ala
            435                 440                 445
Gly Lys Val Thr Lys Ser Ala Gln Lys Ala Gln Lys Ala Lys
            450                 455                 460
```